US008439820B2

(12) United States Patent
MacLean et al.

(10) Patent No.: US 8,439,820 B2
(45) Date of Patent: *May 14, 2013

(54) SYSTEMS AND METHODS FOR SLING DELIVERY AND PLACEMENT

(75) Inventors: Brian MacLean, Acton, MA (US);
James Goddard, Pepperell, MA (US);
Michael S. H. Chu, Brookline, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1388 days.

This patent is subject to a terminal disclaimer.

(21) Appl. No.: 11/147,522

(22) Filed: Jun. 8, 2005

(65) Prior Publication Data

US 2005/0277807 A1 Dec. 15, 2005

Related U.S. Application Data

(63) Continuation-in-part of application No. 11/122,712, filed on May 5, 2005, now Pat. No. 8,142,345.

(60) Provisional application No. 60/578,520, filed on Jun. 9, 2004, provisional application No. 60/569,300, filed on May 6, 2004.

(51) Int. Cl.
*A61F 2/00* (2006.01)

(52) U.S. Cl.
USPC .............................. 600/37; 600/30

(58) Field of Classification Search .......... 600/37, 600/29–31; 606/1, 151–158
See application file for complete search history.

(56) References Cited

U.S. PATENT DOCUMENTS

| 5,337,736 | A | 8/1994 | Reddy | |
|---|---|---|---|---|
| 6,221,005 | B1* | 4/2001 | Bruckner et al. | 600/30 |
| 6,273,852 | B1* | 8/2001 | Lehe et al. | 600/30 |
| 6,382,214 | B1 | 5/2002 | Raz et al. | |
| 6,475,139 | B1* | 11/2002 | Miller | 600/135 |
| 6,478,727 | B2* | 11/2002 | Scetbon | 600/30 |
| 6,494,887 | B1 | 12/2002 | Kaladelfos | |
| 6,502,578 | B2 | 1/2003 | Raz et al. | |
| 6,612,977 | B2 | 9/2003 | Staskin et al. | |
| 6,638,209 | B2 | 10/2003 | Landgrebe | |
| 6,641,525 | B2 | 11/2003 | Rocheleau et al. | |
| 6,652,450 | B2 | 11/2003 | Neisz et al. | |
| 6,685,629 | B2* | 2/2004 | Therin | 600/37 |
| 6,752,814 | B2* | 6/2004 | Gellman et al. | 606/148 |
| 6,802,807 | B2 | 10/2004 | Anderson et al. | |

(Continued)

FOREIGN PATENT DOCUMENTS

WO WO 2004/019786 3/2004

OTHER PUBLICATIONS

Petros, et al., "Urethral Pressure Increase on Effort Originates From Within the Urethra, and Continence From Musculovaginal Closure," Neurology and Urodynamics, 14(4):337-350 (1995).

(Continued)

*Primary Examiner* — Christine Matthews
*Assistant Examiner* — Catherine E Burk
(74) *Attorney, Agent, or Firm* — Bingham McCutchen LLP

(57) ABSTRACT

The invention, in various embodiments, is directed to systems, devices, and methods relating to pre-pubic approaches to delivering a supportive sling to periurethral tissue of a patient.

10 Claims, 17 Drawing Sheets

U.S. PATENT DOCUMENTS

| | | | |
|---|---|---|---|
| 6,808,486 B1 * | 10/2004 | O'Donnell | 600/30 |
| 6,911,003 B2 | 6/2005 | Anderson et al. | |
| 6,960,160 B2 * | 11/2005 | Browning | 600/37 |
| 7,364,541 B2 * | 4/2008 | Chu et al. | 600/30 |
| 2002/0099259 A1 * | 7/2002 | Anderson et al. | 600/29 |
| 2002/0147382 A1 | 10/2002 | Neisz et al. | |
| 2002/0156488 A1 * | 10/2002 | Gellman et al. | 606/139 |
| 2002/0161382 A1 | 10/2002 | Neisz et al. | |
| 2003/0171644 A1 * | 9/2003 | Anderson et al. | 600/29 |
| 2003/0176875 A1 | 9/2003 | Anderson et al. | |
| 2004/0087970 A1 | 5/2004 | Chu et al. | |
| 2005/0177022 A1 * | 8/2005 | Chu et al. | 600/30 |
| 2005/0256366 A1 * | 11/2005 | Chu | 600/30 |

OTHER PUBLICATIONS

Petros, "Ambulatory Surgery for Urinary Incontinence and Vaginal Prolapse," Medical Journal of Australia, 161:171-172 (1994).

Petros, "Medium-Term Follow-Up of the Intravaginal Slingplasty Operation Indicates Minimal Deterioration of Urinary Continence With Time," Aust Nz J Obstet Gynaecol., 39(3):354-356 (1999).

Petros, et al., "An Integral Theory and its Method for the Diagnosis and Management of Female Urinary Incontinence," Scandinavian J. Urology and Nephrology, Supplement 153:193 (1993).

Petros, "An Integral Theory of Bladder Neck Opening, Closure and Urinary Incontinence in the Female," International Journal of Gynecology & Obstetrics, XXIII World Congress of Gynecology and Obstetrics (Figo) (1991).

Petros, "The Intravaginal Slingpasty Operation, A Minimally Invasive Technique for Cure of Urinary Incontinence in the Female," Aust. Nz J. Obstet Gynaecol., 36(4):453-461 (1996).

Ulmsten, et al, "Intravaginal Slingplasty (IVS): An Ambulatory Surgical Procedure for Treatment of Female Urinary Incontinence," Scand J. Urology Nephrol 29(1):75-82 (1995).

Ulmsten, et al., "A Multicenter Study of Tension-Free Vaginal Tape (TVT) for Surgical Treatment of Stress Urinary Incontinence," Int Urogynecol J., 9(4):210-213 (1998).

Ulmsten, et al., "A Three-Year Follow Up of Tension Free Vaginal Tape for Surgical Treatment of Female Stress Urinary Incontinence," British J. of Obstetrics and Gyn., 106:345-350 (1999).

Ulmsten, et al., "An Ambulatory Surgical Procedure Under Local Anesthesia for Treatment of Female Urinary Incontinence," The International Urogynecology Journal, 7:81-86 (1996).

Ulmsten, et al., "An Introduction to Tension-Free Vaginal Tape (TVT)—A New Surgical Procedure for Treatment of Female Urinary Incontinence," Int. Urogynecol J. (Suppl 2):S3-4 (2001).

Ulmsten, et al., "Connective Tissue Factors in the Aeticology of Female Pelvic Disorders," Ann. Med., 22(6):3 (1990).

Ulmsten, et al., "Intravaginal Slingplasty," Zentralbl Bynakol., 116:398-404 (1994).

Ulmsten, et al., "Surgery for Female Urinary Incontinence," Current Opinion in Obstetrics & Gynecology, 4(3):456-462 (1992).

Ulmsten, "The Basic Understanding and Clinical Results of Tension-Free Vaginal Tape for Stress Urinary Incontinence," Der Urologe, [A] 40:269-273 (2001).

* cited by examiner

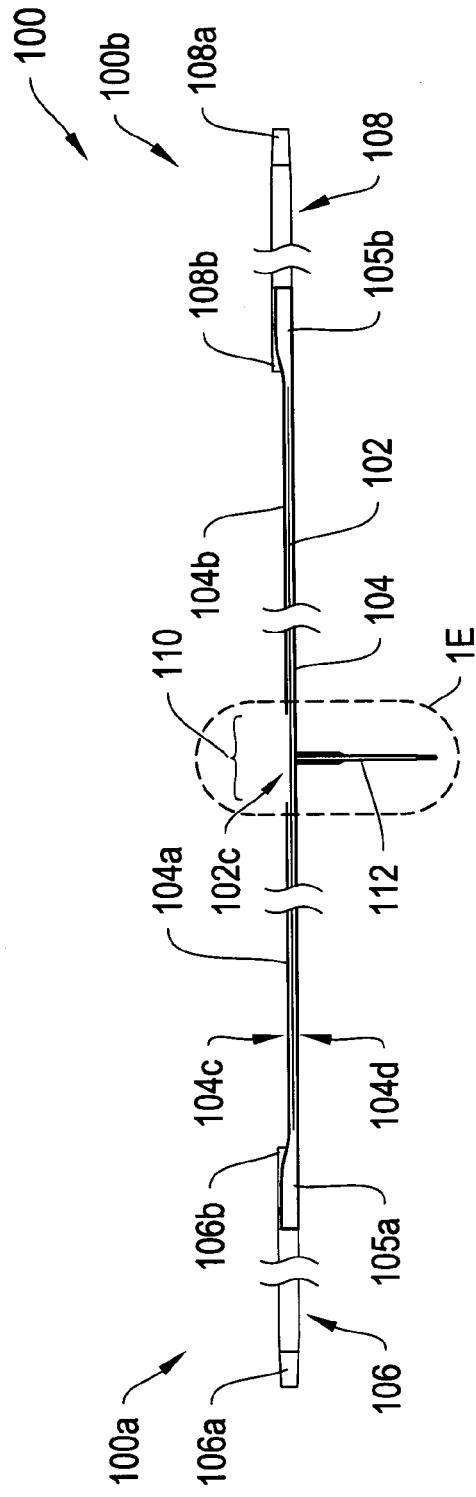
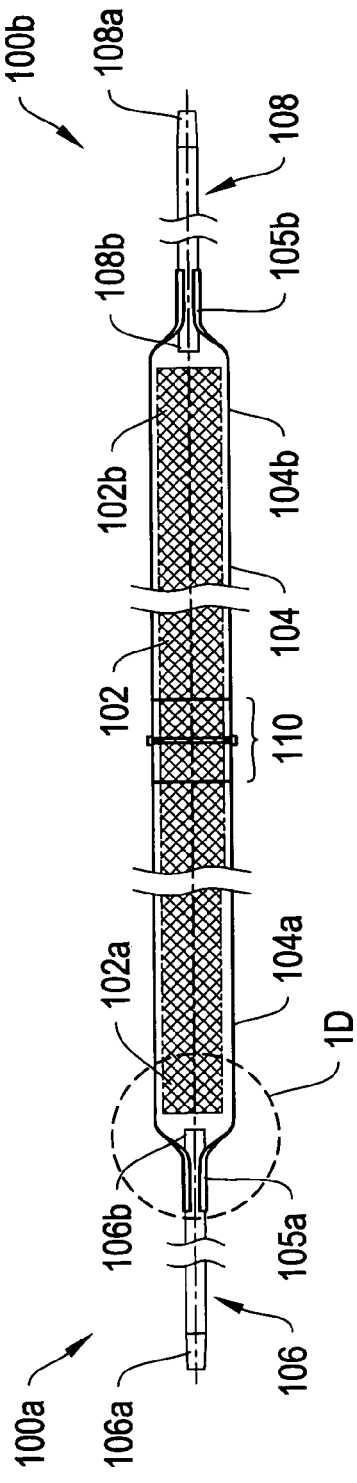
Figure 1A
Figure 1B

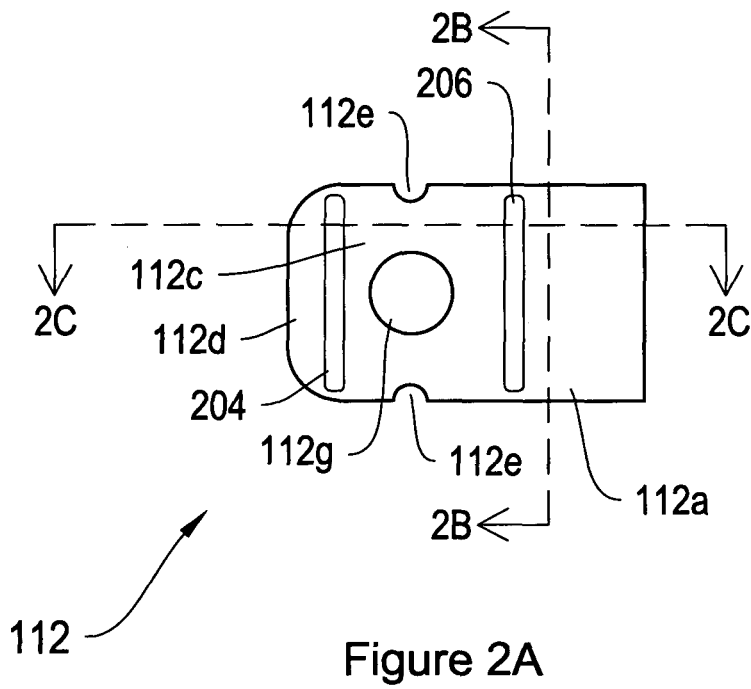
Figure 2A
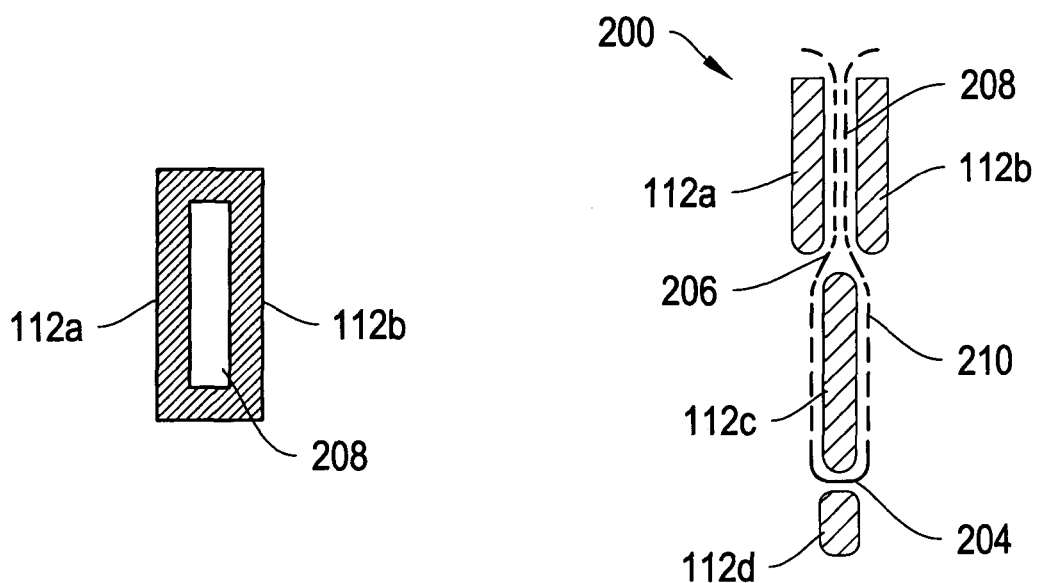
Figure 2B
Figure 2C

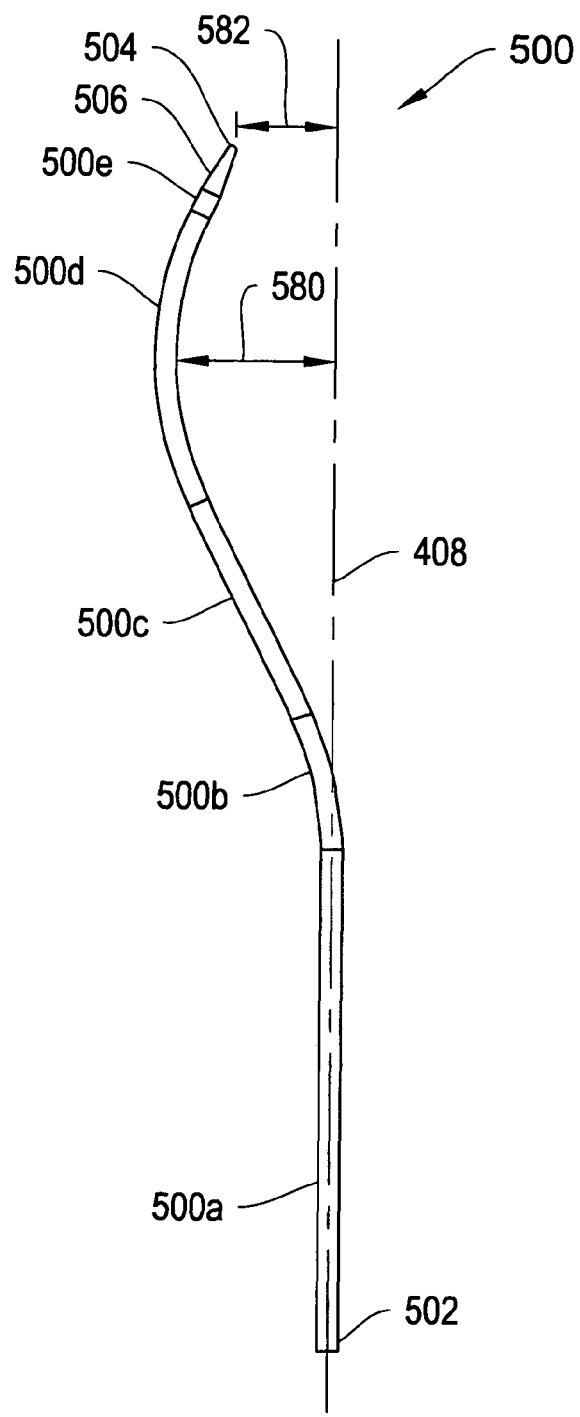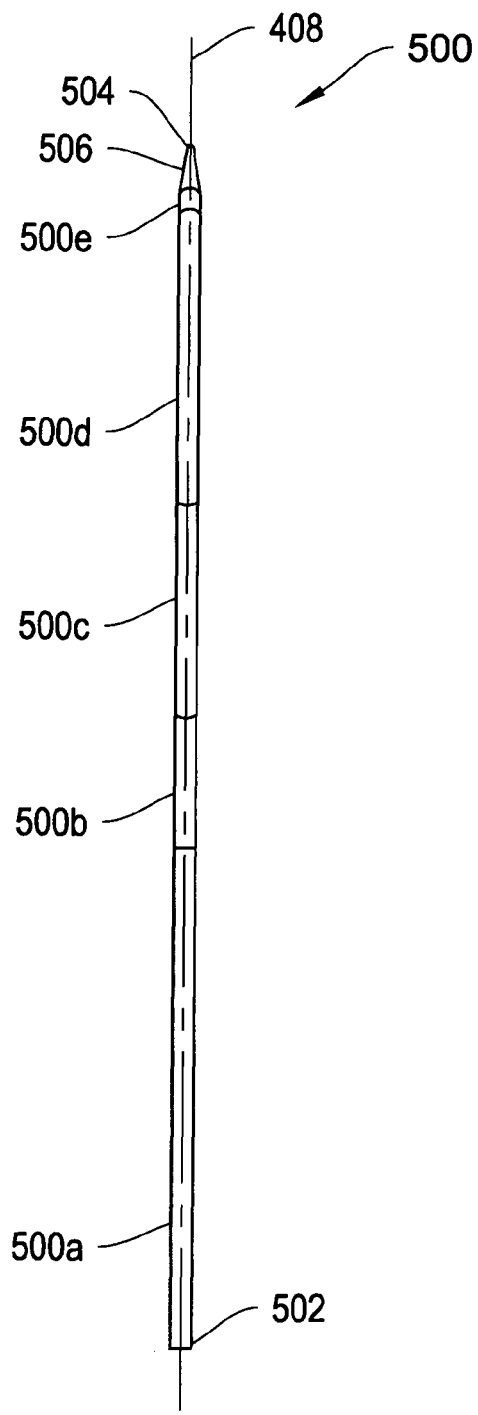
Figure 5A
Figure 5B

SYSTEMS AND METHODS FOR SLING DELIVERY AND PLACEMENT

CROSS REFERENCE TO RELATED APPLICATIONS

This application claims the benefit of and priority to U.S. Provisional Patent Application Ser. No. 60/578,520 filed on Jun. 9, 2004, which is hereby incorporated by reference in its entirety. This is a continuation-in-part of U.S. patent application Ser. No. 11/122,712, filed, May 5, 2005 now U.S. Pat. No. 8,142,345, which claims priority from U.S. Provisional Patent Application No. 60/569,300, filed May 6, 2004.

FIELD OF THE INVENTION

The invention generally relates to systems and methods for delivering a supportive sling to an anatomical location in a patient. In various embodiments, the invention is directed to systems, devices, and methods relating to prepubic placement of a supportive sling to the periurethral tissue of a patient to treat urinary incontinence.

BACKGROUND OF THE INVENTION

Anatomical tissues may become weakened or damaged by age, injury, or disease. This decrease in the structural integrity of anatomical tissues may have significant medical consequences. Even in the absence of tissue necrosis, weakening of an anatomical structure may impair one or more of the biological functions of the tissue. To help alleviate this impact on biological function, implantable, supportive slings have been developed. These slings can be implanted into a patient to provide support for the weakened or damaged tissue. The support provided by the sling mimics the natural position and structure of the tissue, and thereby helps decrease or eliminate impairment of biological function resulting from tissue weakening or damage. Although supportive slings have been used in numerous contexts to address the weakening of a variety of anatomical tissues, they have proven particularly useful for decreasing urinary incontinence resulting from weakening or damage to urethral, periurethral, and/or bladder tissue.

Stress urinary incontinence (SUI) affects primarily women, but also men, and is generally caused by two conditions, intrinsic sphincter deficiency (ISD) and hypermobility. These conditions may occur independently or in combination. In ISD, the urinary sphincter valve, located within the urethra, fails to close properly (coapt), causing urine to leak out of the urethra during stressful activity. Hypermobility is a condition in which the pelvic floor is distended, weakened, or damaged, causing the bladder neck and proximal urethra to rotate and descend in response to increases in intra-abdominal pressure (e.g., due to sneezing, coughing, straining, etc.). As a result, the patient's response time becomes insufficient to promote urethral closure and, consequently, the patient suffers from urine leakage and/or flow. SUI has a variety of causes including, but not limited to, pregnancy, aging, infection, injury, congenital defects, and disease.

A popular treatment of SUI involves placement of an implantable sling under the bladder neck or the mid-urethra to provide a urethral platform. Placement of the sling limits the endopelvis fascia drop. There are various methods for placing the sling. Slings can be affixed and stabilized using traditional bone anchoring approaches, as well as recently developed anchor-less methods. Additionally, a variety of implantation procedures, including various routes of administration, exist. These procedures provide physicians with a range of implantation options. Physicians can readily select amongst the various implantation procedures based on numerous patient-specific factors including, but not limited to, age, gender, overall health, location of tissue defect, the degree of tissue impairment, and the like. Furthermore, physicians can select from amongst numerous sling delivery devices that facilitate sling placement.

Despite the numerous advances in sling design, implantation methodologies, and delivery devices, no single method and/or device is appropriate for every situation. Accordingly, devices, systems, and methods that offer new approaches for sling implantation would be advantageous to the medical community.

SUMMARY OF THE INVENTION

The invention addresses deficiencies of the prior art by, in one embodiment, providing delivery devices, systems, and methods for facilitating prepubic delivery of an implant to an anatomical site in a patient. In particular, the invention provides delivery devices, systems, and methods for placing a sling for treating urinary incontinence, including SUI, by a trans-vaginal, prepubic approach.

In one aspect, the invention provides a sling delivery system having a sling assembly including an implantable sling, sized and shaped for providing a urethral platform. Optionally, the sling assembly includes a sleeve for covering, at least partially, the sling. In embodiments including a sleeve, the sling is preferably free floating inside the sleeve and does not attach to the sleeve or anything else. The sleeve may have a gap exposing a portion of the sling. In certain embodiments, the gap is between about 1 cm and about 3 cm in length. The sleeve includes a looped portion, covered at least partially by a tab, extending out of the plane of the sleeve and the sling. In some embodiments, the tab prevents the sleeve from being removed from the sling, and cutting the tab permits sleeve removal. According to one embodiment, the sling assembly also includes first and second guide tubes, possessing longitudinally extending through lumens and located at first and second ends of the sling assembly. In some embodiments, the lumens have a diameter of less than 0.63 cm, such as less than 0.5 cm or less than 0.3 cm. In preferred embodiments, the guide tubes are between about 15 cm and about 18 cm in length. In some embodiments, the guide tubes attach to ends of the sleeve. In other embodiments, the guide tubes also or alternatively attach to ends of the sling.

The sling delivery system also provides a delivery device for prepubicly delivering a supportive sling to the periurethral tissue of a patient. In one embodiment, the delivery device includes a handle and a shaft extending from a distal end of the handle. The shaft may include one or more substantially straight sections and/or one or more curved sections. In some configurations, the shaft and the handle are substantially in the same plane. In other configurations, at least one section of the shaft and the handle are located in different planes. In some configurations, the shaft is located substantially in one plane. In other configurations, the shaft includes sections located in different planes. In some embodiments, the shaft has a conical tip and is sized and shaped for slidably interfitting within the lumen of one or both of the guide tubes of the sling assembly. According to one configuration, the shaft has a distal portion that extends between about 1 cm to about 5 cm across an axis created by a straight section of the shaft. According to another configuration, the shaft is between about 17 cm and about 23 cm in length, including the tip. In some embodiments, the shaft has an outside diameter less than about 0.63 cm, for example less than about 0.5 cm or less than about 0.3 cm. In certain embodiments, the shaft has a substantially constant diameter. In some configurations, the shaft and the guide tubes are sized and shaped to enable a medical operator to grasp an outer (distal end) of a guide tube and withdraw the delivery device to disassociate the shaft of the delivery device from the guide tube, for example, with need of a pusher assembly. In other embodiments, the delivery device includes a pusher assembly for facilitating removal of the shaft from the guide tubes. According to one feature, the pusher assembly can slidably advance coaxially along a portion of the shaft.

According to one method of use, the shaft of the delivery device is employed to create passages through body tissue, namely, from the vagina over the anterior surface of the pubic bone through the abdominal fascia to the abdomen. According to one approach, three incisions are made in the body of the patient. One incision on each side of the midline of the body is made in the lower abdomen and a third incision is made in the anterior vaginal wall. A first one of the guide tubes is fitted over the shaft of the delivery device. The delivery device with the guide tube installed is inserted through the vaginal opening to one side of the urethra, for example, along the anterior side of the pubic bone between the ischiocavamous pubic muscle and the ischiopubic bone until the conical tip of the shaft is exposed through one of the abdominal incisions. A medical operator may then grasp or otherwise temporarily secure the exposed end of the guide tube and withdraw the delivery device to leave the first guide tube and at least a portion of the sling assembly within the body of the patient. These steps may then be repeated on the contralateral side of the body.

According to another approach, as the delivery device with the guide tube installed is advanced along the anterior side of the pubic bone, it may be rotated in a clockwise or counter clockwise direction about 30 degrees, about 60 degrees, about 90 degrees, about 180 degrees to facilitate the distal end of the shaft exposing itself at a particular location in the abdomen of the patient. According to a further approach, a pusher assembly of the delivery device may be pushed distally from the handle to advance an end of the guide tube beyond the conical tip of the shaft to make it easier for the medical operator to grasp or otherwise temporarily secure.

Subsequent to placement, the guide tubes are withdrawn from the abdominal incision, pulling the ends of the sling assembly through the passages created by the shaft. The guide tubes may be used as handles to adjust the position of the sling assembly to achieve desired placement. In the case where no sleeve is used, the guide tubes are detached from the sling ends, for example, by cutting or other suitable approach. In the case where a sleeve is employed, once desired placement of the sling assembly is achieved, the tab is cut to separate the plastic sleeve into two portions. By pulling on the guide tubes, the plastic sleeve is slid off the sling and removed from the body. The guide tubes and/or the plastic sleeve are then discarded. If necessary, the ends of the sling are cut to a desired length to facilitate placement of the sling, for example, under the urethra. Optionally, the sling may be anchored at any suitable location. In one embodiment, the sling ends are anchored between the ischiocavemous pubic muscles and ischiopubic bone.

Additional features and advantages of the invention will be apparent from the following description of preferred embodiments and from the claims.

BRIEF DESCRIPTION OF THE DRAWINGS

The following figures depict certain illustrative embodiments of the invention in which like reference numerals refer to like elements. These depicted embodiments may not be drawn to scale and are to be understood as illustrative of the invention and not as limiting in any way.

FIGS. 1A-1B depict side and top views, respectively, of a sling assembly according to an illustrative embodiment of the invention.

FIGS. 2A-2C depict more detailed views of one embodiment of a tab according to an illustrative embodiment of the invention

FIGS. 5A-5B depict different views of another embodiment of a shaft of a delivery device for delivering a sling to an anatomical site of a patient according to an illustrative embodiment of the invention.

ILLUSTRATIVE DESCRIPTION

Figure 1C:
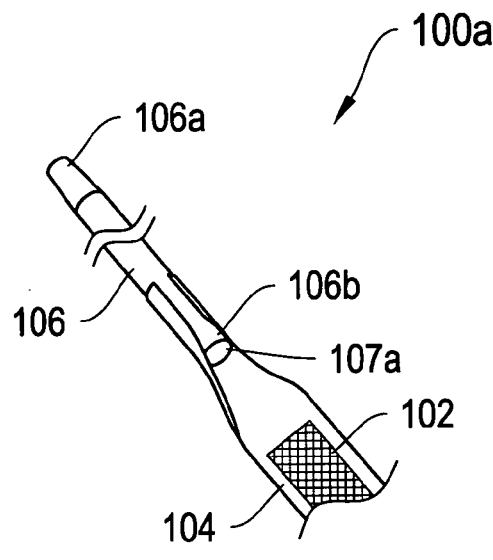
FIGS. 1C-1F depict more detailed views of the sling assembly of FIGS. 1A-1B.

As described in summary above, the invention, in one illustrative embodiment, relates to systems and methods for delivering and placing a medical implant at an anatomical site in the body of a patient. In particular, in various illustrative examples, the invention provides delivery devices, systems, and methods for placing an implant, e.g., a sling for treating urinary incontinence, including SUI, by a trans-vaginal approach. In one aspect, the invention provides a delivery device for prepubicly delivering a supportive sling to the periurethral tissue of a patient. In one embodiment, the delivery device includes a handle and a shaft extending from a distal end of the handle. The patient may be either a female patient or a male patient, but is described below for illustrative purposes as being female.

In one illustrative embodiment, the invention provides simplified systems and methods for delivering and placing a medical implant to an anatomical site of a patient, with reduced trauma to the patient. According to one advantage, the systems and methods of the invention may reduce the need for any cystoscopy during sling placement. According to a further advantage, the invention also avoids the need for entering the retropubic space during sling placement, hence reducing the dangers of bladder and/or bowel puncture. This also allows a medical operator to deliver and place a medical implant to an anatomical site of a patient who has experienced problems with a medical implant placed in the retropubic space. According to a further advantage, the invention also avoids the need for any bone anchors to anchor the sling in place. According to another advantage, the invention allows the medical operator implanting the medical device to feel the delivery device under the surface of the skin, thereby, enabling the medical operator to more accurately guide and place the delivery device and sling assembly.

Without limitation, exemplary delivery systems, slings, sling attachments and methodologies that may be employed in combination with the invention can be found in U.S. Pat. No. 6,755,781, entitled "Medical Slings," U.S. Pat. No. 6,666,817, entitled "Expandable Surgical Implants and Methods of Using Them," U.S. Pat. No. 6,669,706, entitled "Thin Soft Tissue Surgical Support Mesh," U.S. Pat. No. 6,375,662, entitled "Thin Soft Tissue Surgical Support Mesh," U.S. Pat. No. 6,042,592, entitled "Thin Soft Tissue Surgical Support Mesh," U.S. patent application Ser. No. 10/015,114, entitled "Devices for Minimally Invasive Pelvic Surgery," U.S. patent application Ser. No. 10/774,826, entitled "Devices for Minimally Invasive Pelvic Surgery," U.S. patent application Ser. No. 10/093,398, entitled "System for Implanting an Implant and Method Thereof," U.S. patent application Ser. No. 10/093,498, entitled "System for Implanting an Implant and Method Thereof," U.S. patent application Ser. No. 10/093,371, entitled "System for Implanting an Implant and Method Thereof," U.S. patent application Ser. No. 10/093,424, entitled "System for Implanting an Implant and Method Thereof," U.S. patent application Ser. No. 10/093,450, entitled "System for Implanting an Implant and Method Thereof," U.S. patent application Ser. No. 10/094,352, entitled "System for Implanting an Implant and Method Thereof," U.S. patent application Ser. No. 10/631,364, entitled "Bioabsorbable Casing for Surgical Sling Assembly," U.S. patent application Ser. No. 10/641,376, entitled "Spacer for Sling Delivery System," U.S. patent application Ser. No. 10/641,487, entitled "Systems, Methods and Devices Relating to Delivery of Medical Implants," U.S. patent application Ser. No. 10/642,395, entitled "Systems, Methods and Devices Relating to Delivery of Medical Implants," U.S. patent application Ser. No. 10/642,397, entitled "Systems, Methods and Devices Relating to Delivery of Medical Implants," U.S. patent application Ser. No. 10/832,653, entitled "Systems and Methods for Sling Delivery and Placement," U.S. patent application Ser. No. 10/939,191, entitled "Devices for Minimally Invasive Pelvic Surgery," U.S. Provisional Patent Application Ser. No. 60/508,600, filed on Oct. 3, 2003, U.S. Provisional Patent Application Ser. No. 60/578,520, filed on Jun. 9, 2004, U.S. Provisional Patent Application Ser. No. 60/569,300, filed on May 6, 2004, U.S. patent application Ser. No. 10/642,365, entitled "Systems, Methods and Devices Relating to Delivery of Medical Implants," and U.S. patent application Ser. No. 10/957,926, entitled "Systems and Methods for Delivering a Medical Implant to an Anatomical Location in a Patient," filed on Oct. 4, 2004, the entire contents of all of which are incorporated herein by reference. All operative combinations between illustrative embodiments described herein and those features described in the disclosure of references are considered to be potentially patentable embodiments of the invention.

FIG. 1A shows a side view of a sling assembly 100 of the type employed with the invention. As shown, the sling assembly 100 has first 100a and second 100b ends. According to the illustrative embodiments, the distance between first 100a and second 100b ends is from about 70 cm to about 95 cm, for example, from about 80 cm to about 85 cm. The sling assembly 100 includes a knitted mesh or sling 102. Optionally, the sling assembly includes a sleeve 104 for covering, at least partially, the sling 102. In embodiments including a sleeve, the sling 102 is preferably free floating inside the sleeve 104. The sleeve 104 has first 104a and second 104b portions, and first and second end portions 105a and 105b. The sling assembly 100 also includes first 106 and second 108 dilator or guide tubes. Each illustrative guide tube 106 and 108 is a flexible polymer tube and is about 15 cm to about 18 cm in length. The guide tubes 106 and 108 have outer ends 106a ad 108a, respectively. As shown in the illustrative embodiment, the outer ends 106a and 108a are tapered, which facilitates dilation of tissues within the body of a patient. In other embodiments, the outer ends 106a and 108a are tapered more or less severely or not at all. The guide tubes 106 and 108 also include inner ends 106b and 108b, respectively. The guide tubes 106 and 108 have longitudinally extending through lumens 107a and 107b, shown in FIG. 1C, which run the length of the guide tubes from outer ends 106a and 108a to inner ends 106b and 108b, respectively. In some embodiments, the inner ends 106b and 108b of the guide tubes 106 and 108 attach to respective sleeve ends. In other embodiments, described below in more detail, the inner ends 106b and 108b attach to respective sleeve ends.

FIG. 1B shows a top view of the sling assembly 100, including a sleeve 104. The sleeve end portion 105a wraps partially around and attaches to the guide tube 106. Attachment may be by any suitable mechanism, including, without limitation, heat bonding, gluing, stapling, stitching, shrink wrapping or the like. The sleeve end portion 105b attaches to the guide tube 108 in a similar fashion. In other illustrative embodiments, the sling end portions 102a and 102b may attach to the guide tubes 106 and 108, respectively, in a similar fashion; that is, the guide tubes 106 and 108 may be directly attached to the ends of the sling 102a and 102b.

As shown in FIGS. 1A and 1B, an opening or gap 110 is located near a midpoint of a top surface 104c of the sleeve 104. The gap 110 exposes a portion 102c of the sling 102 where the entire width of the sling 102 is exposed. In preferred embodiments, the gap is from about 1 cm to about 3 cm in length, such as about 1 cm to about 2 cm in length. In one preferred embodiment, the gap is about 1.5 cm to about 2 cm in length. In other embodiments, the sleeve 104 covers the sling 102 completely. Additionally, in some embodiments, there may be more than one gap along the length of the sleeve 104 where the sling 102 is not covered by the sleeve 104.

FIG. 1A further depicts a tab or spacer 112 near a midpoint of a bottom surface 104d of the sleeve 104. In illustrative embodiments, the tab is located from about 22 cm to about 25 cm away from one or both inner guide tube ends 106a and 108a. In preferred embodiments, the tab 112 is from about 1 cm to about 3 cm in length, such as about 2 cm to about 2.5 cm in length. In some embodiments, the tab 112 extends away from the plane of the sleeve portions 104a and 104b and the sling 102. In the illustrative embodiment, the tab extends at about a 90 degree angle from the plane of the sleeve portions 104*a* and 104*b* and the sling 102. In other illustrative embodiments, the tab extends at about a 80, 60, or 30 degree angle from the plane of the sleeve portions 104*a* and 104*b* and the sling 102. Although the gap 110 and the tab 112 are shown at the mid-point of the sleeve 104, in other illustrative embodiments, the gap 110 and the tab 112 may be near the mid-point of sleeve 104, but not at the mid-point, or even substantially off-set from the mid point. The tab 112 is discussed further below.

FIG. 1C shows a perspective view of the first end 100*a* of the sling assembly 100. The longitudinally extending through lumen 107*a* runs the length of the guide tube 106. Similarly, the lumen 107*b* runs the length of the tube 108. In some embodiments, the lumens 107*a* and 107*b* have a uniform diameter. In preferred embodiments, the lumens have a diameter of less than 0.63 cm, such as less than or equal to 0.5 cm, or even less than or equal to 0.3 cm. In other embodiments, the lumens 107*a* and 107*b* have one or more locations of increased and/or decreased diameter. For example, the guide tube walls, which define the lumens 107*a* and 107*b*, may have bumps, ridges, shoulders, grooves, or other internal protuberances, which may increase or decrease the size of the lumens 107*a* and 107*b*. The lumens 107*a* and 107*b* are sized and shaped to slidably interfit over the shaft of a delivery device, which is discussed in detail below. The lumens 107*a* and 107*b* may have one or more portions, with decreased diameter to reduce the ability of the shaft of a delivery device to slide through the lumens. In some embodiments, such portions of reduced diameter may be located near the outer ends 106*a* and 108*a* of the guide tubes 106 and 108, respectively.

Figure 1D:
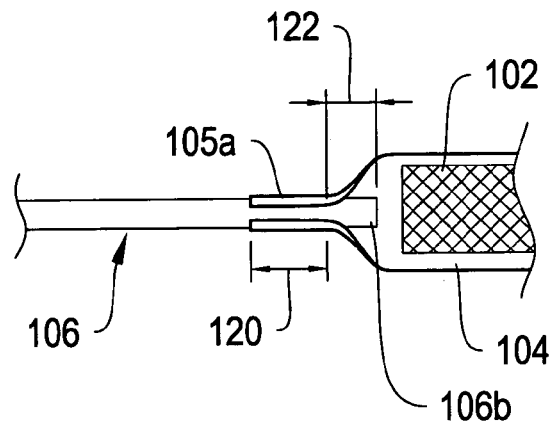

FIG. 1D shows a more detailed rendering of the portion of the sling assembly 100 marked by the dotted line ID in FIG. 1B. As shown in the illustrative embodiment, the guide tube 106 is attached to the first end portion 105*a* of the sleeve 104. In preferred embodiments, the distance 120 of attachment of the first end portion 105*a* to the guide tube 106 is from about 0.5 cm to about 2 cm, for example, from 1 cm to about 1.5 cm. In preferred embodiments, the distance 122 from the nearest point of attachment of the first end portion 105*a* to the inner end 106*b* of the guide tube 106 is about at least 0.65 cm.

Figure 1E:
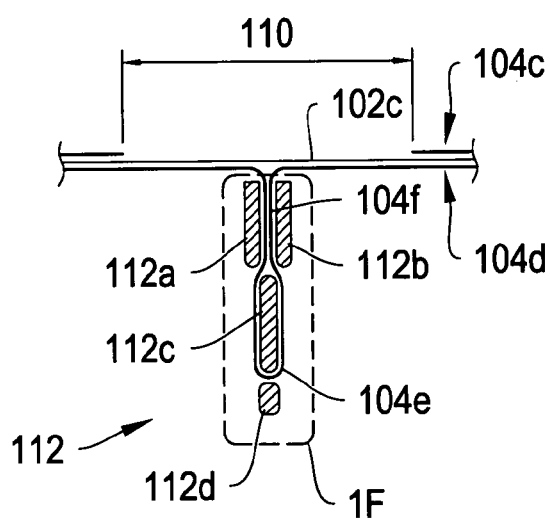
Figure 1F:
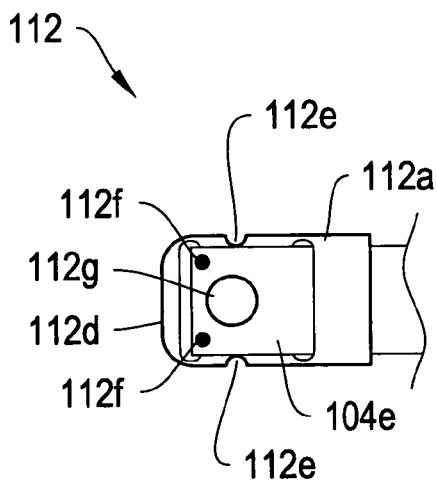

FIGS. 1E-1F show views of the region of sling assembly 100 marked by the dotted line 1E in FIG. 1A, which includes the tab 112. Views of the tab 112 are also shown in FIGS. 2A-2C. Referring to FIGS. 1A-1B and 1E-1F, the sleeve portions 104*a* and 104*b* are formed as an integral sleeve 104 having a continuous bottom side 104*d*. The bottom side 104*d* includes a looped portion formed from looped sections 104*e* and 104*f*. The looped sections 104*e* and 104*f* of the sleeve 104 extend downward out of the plane of the sleeve portions 104*a* and 104*b* and the sling 102, for example, at an angle of about 90 degrees. The looped sections 104*e* and 104*f* are covered, at least partially, by the tab 112, which fits over the looped sections. In other embodiments, the sleeve portions 104*a* and 104*b* may be separate sections fastened to each other by the tab 112 on the bottom side 104*d*.

According to the illustrative embodiment of FIG. 1E, the tab 112 has two wall sections 112*a* and 112*b* which enclose the looped section 104*f* of the sleeve 104. The tab 112 also includes a body section 112*c*, which is circumscribed by looped section 104*e* of the sleeve 104. The tab 112 also includes an end section 112*d* which, along with body section 112*c*, forms a first through slit 204 (seen in FIG. 2A) through which the looped section 104*e* of the sleeve 104 passes. As shown, the wall sections 112*a* and 112*b* in combination with the body section 112*c* form a second through slit 206 (seen in FIG. 2A) through which the looped section 104*f* of the sleeve 104 passes.

According to the illustrative embodiment of FIG. 1F, the looped section 104*e* of sleeve 104 circumscribes the body section 112*c* of tab 112. The looped section 104*e* of sleeve 104 is heat bonded to the body section 112*c* of tab 112 at bonding locations 112*f*. In other embodiments, attachment is by any other suitable mechanism, including, without limitation, gluing, stapling, stitching, shrink wrapping or the like. The body section 112*c* includes an aperture 112*g* near the middle of its width. In preferred embodiments, the sleeve 104 and the looped section 104*e* is clear and/or transparent and the aperture 112*g* can be visualized by the medical operator when it is covered by the looped section 104*e*. The body section 112*c* of the tab 112 also includes two indentations 112*e* on opposite sides of the aperture 112*g*. The indentations 112*e* and the aperture 112*g* of the tab 112 serve as visual indicators for the medical operator when cutting through the tab 112 during the implantation procedure.

FIG. 2A shows a side view of tab 112, analogous to FIG. 1E, where sleeve 104 is absent. As shown in the illustrative embodiment, the aperture 112*g* is located at a substantially middle portion of the body section 112*c*. The indentations 112*e* are on opposite sides of the aperture 112*g*. When present, the looped section 104*e* of the sleeve 104 emerges from behind the wall section 112*a* at the second through slit 206. The looped section 104*e* then covers the middle portion 112*c* and loops through the first through slit 204 to the opposite side of the tab.

As shown in the illustrative embodiment of FIG. 2B, the wall sections 112*a* and 112*b* bind a channel space 208. When the sleeve 104 is fitted with the tab 112, the looped section 112*f* is within the space 208.

As shown in the illustrative embodiment of FIG. 2C, wall sections 112*a* and 112*b* bind the channel space 208. The second through slit 206 lies between the wall sections 112*a* and 112*b* and the body section 112*c*. The first through slit 204, lies between the body section 112*c* and the end section 112*d*. The path traced by the looped sections 104*e* and 104*f* of the sleeve 104, when present, is depicted by the dotted line 210.

The tab 112 can also be used during implantation as a visual aid for placement of the sling 102. According to the illustrative embodiment, the tab 112 inhibits, or in some embodiments, prohibits the sleeve 104 from sliding off, or otherwise being removed from, the sling 102 during sling assembly placement. Preferably, the tab 112 must be cut to enable the sleeve 104 to slide off the sling 102. According to one embodiment, cutting the tab 112 enables the sleeve portions 104*a* and 104*b* to be slid off the sling ends 102*a* and 102*b*, respectively. This feature ensures that the sleeve 104 cannot be removed simply by applying a pulling force, for example, to the sleeve end sections 105*a* and 105*b* or to the tab 112. Such a force may be applied to the sling assembly 100 by a medical operator during sling assembly placement.

During placement, after the sling assembly 100 is positioned within the patient, a cut is made through the center of the tab 112, across indentations 112*f*, through aperture 112*g*, and thus through the looped section 104*e* of the sleeve 104, allowing the two sleeve portions 104*a* and 104*b* to be separated from each other. The sleeve portions 104*a* and 104*b* are then slid off of the sling 102, out of the body of the patient by pulling on the two sleeve portions 104*a* and 104*b*, the sleeve end portions 105*a* and 105*b*, the two guide tubes 106 and 108, or generally on the two ends 100*a* and 100*b* of the sling assembly 100. Further details regarding the tab 112 and other mechanisms of fastening the sleeve portions 104*a* and 104*b* are provided in the co-pending U.S. patent application Ser. No. 10/642,395 entitled "Systems, Methods and Devices Relating to Delivery of Medical Implants," the entire disclosure of which is incorporated by reference herein.

The sleeve 104 may be made, for example, from one or more absorbent materials, such as a sponge-like material, which can optionally be pre-soaked in a drug solution, for example, in an anesthetic, anti-inflammatory, coagulating, anticoagulating, and/or antibiotic solution. In other embodiments, the sleeve 104 may be made from a non-wettable material, such as polypropylene, polyethylene, polyester, polytetrafluoroethylene (available from DuPont Corporation, Wilmington, Del., under the trademark TEFLON®), TYVEK®, MYLAR®, or co-polymers thereof. The non-wettable materials can also be pretreated with a therapeutically effective drug treatment. The sleeve 104 is preferably transparent so that an operator can to see the sling 102 inside the sleeve 104. In some embodiments, the sling 102 and/or sleeve 104 may be colored to facilitate placement of the sling by the operator. The sleeve 104 may include both transparent and colored sections.

According to the illustrative embodiment, the sling 102 is from about 1 cm to about 3 cm in width and from about 10 cm to about 45 cm in length, and terminates at free ends. In some embodiments, the sling is about 1 cm in width and about 45 cm in length. In other embodiments, the sling 102 is about 5 cm, between about 5 cm and about 10 cm, between about 10 cm and about 15 cm, between about 15 cm and about 20 cm, between about 20 cm and about 25 cm or between about 25 cm and about 30 cm. The sling 102 is shown to be rectangular, but it may have another suitable shape. The sling 102 may have a uniform thickness over its entire length and/or width. Alternatively, the thickness can be suitably varied at one or more locations. According to the illustrative embodiment, the thickness of the sling 102 material ranges from about 0.02 cm to about 0.10 cm.

According to the illustrative embodiment, in configurations using a sleeve 104, the length of the sling 102 is shorter than the length of the sleeve 104, and the sling 102, including both ends 102a and 102b, does not connect to the sleeve 104 or anything else. During sling assembly placement, this feature enables a medical operator to pull on the sling assembly ends 100a and 100b, for example, via the guide tubes 106 and 108, and/or any of the delivery devices to be used for placement, without risk of stretching, curling, tensioning, or otherwise deforming the sling 102. In particular, this feature inhibits the medical operator from gripping the free ends of the sling, and this feature may be further enhanced by making the sling 102 long enough to support the urethra, but not long enough to expose the ends 102a and 102b of the sling outside the body. This has the added advantage of preventing infection caused by the exposure of the sling 102 external to the body. By way of example, an illustrative sleeve 104 is about 1 cm, 2 cm, 3 cm, 4 cm, 5 cm, 6 cm, 7 cm, 8 cm, 9 cm, or 10 cm longer than the sling 102. According to other illustrative embodiments, the sleeve 104 is about 10 cm, 15 cm, 20 cm, 25 cm, or 30 cm longer than the sling 102. In other embodiments, the sling 102 is configured in length to extend outside of the body, when placed, and the ends then trimmed to length by the medical operator to a point just under the skin.

In the illustrative embodiment, the sling 102 is made entirely of polypropylene. However, sling 102 may be fabricated from any of a number of biocompatible materials, such as nylon, polyethylene, polyester, polypropylene, fluoropolymers, copolymers thereof, combinations thereof, or other suitable synthetic material(s). The material may be, for example, a synthetic material that is absorbable by the patient's body, such as polyglycolic acid, polylactic acid, and other suitable absorbable synthetic materials. Alternatively, the material for the sling 102 may be derived from mammalian tissue(s) or a combination of mammalian tissue(s) and synthetic material(s). The sling material may be fabricated from one or more yarns, which yarns may be made from one or more materials. The sling 102 may incorporate or be coated with one or more agents to provide a therapeutic effect, for example, to reduce discomfort, to reduce the chance of infection and/or to promote tissue growth.

In one illustrative embodiment, the edge regions of the sling 102 can be configured differently depending on their intended placement in the body of the patient. For example, a midsection of the sling is typically located where an anatomical site, such as a mid-urethral or bladder neck location in the periurethral tissue, needs to be supported. In one illustrative embodiment, the midsection of the sling 102 has smooth or rounded edges, hereinafter also referred to as "non-tanged" or "de-tanged." According to a further illustrative embodiment, other sections of the sling may include tangs (e.g., sharp projections or frayed edges). The tangs are generally useful for anchoring the sling 102, for example, into the ischiopubic tissues, and/or encouraging tissue growth into the sling. Anchoring the sling 102 in this manner generally obviates the need for additional sutures to hold the sling in place.

The tanged and non-tanged edges of the sling 102 can be formed in a plurality of ways. For example, the sling 102 can be cut from a woven sheet, in which case the edges would be initially tanged along the entire length of the sling. One or more non-tanged sections may be formed by any process that smoothes, rounds or removes the sharp edges of the tangs. For example, the tangs may be heat-smoothed by burning or melting the tangs. In one embodiment, the non-tanged section has a length of about 1 cm to about 5 cm, preferably about 2 cm to about 2.5 cm, on either or both sides of the center line of the sling. Providing one or more non-tanged sections, which may be in close proximity to a sensitive anatomical site in the patient, can enhance the comfort level of the patient and reduce the potential for the edges of the tangs to erode or irritate the urethra. Alternatively, the sling 102 can be produced from a woven tape having the approximate finished width of the sling. The smooth sides of the tape can then be trimmed off to produce the tanged sections.

Figure 3A:
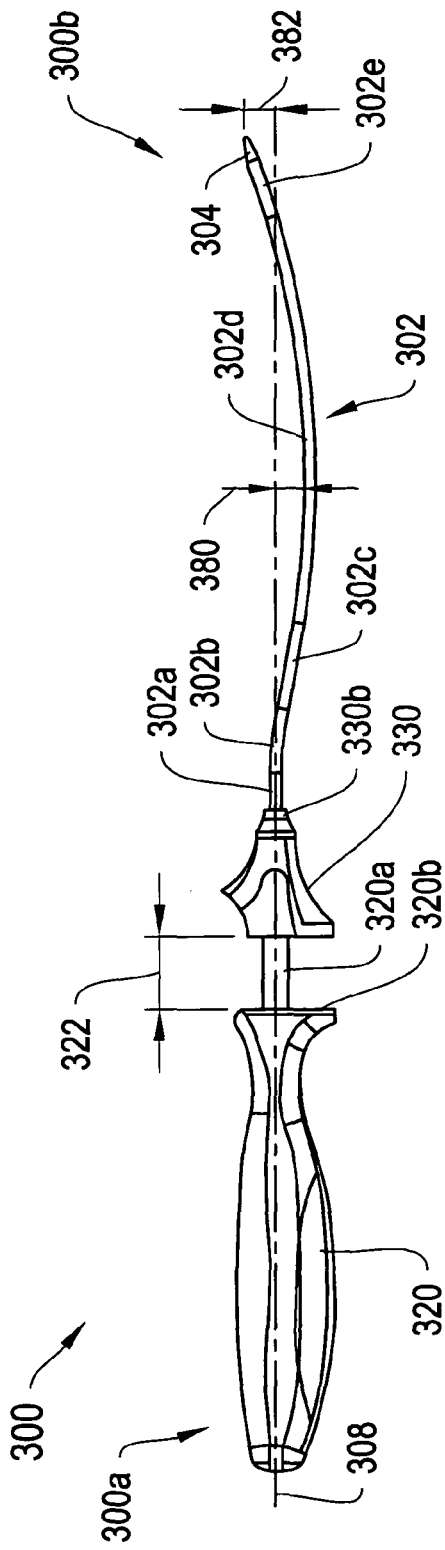
FIGS. 3A-3B depict side and top views, respectively, of one embodiment of a delivery device for delivering a sling to an anatomical site of a patient according to an illustrative embodiment of the invention.
Figure 3B:
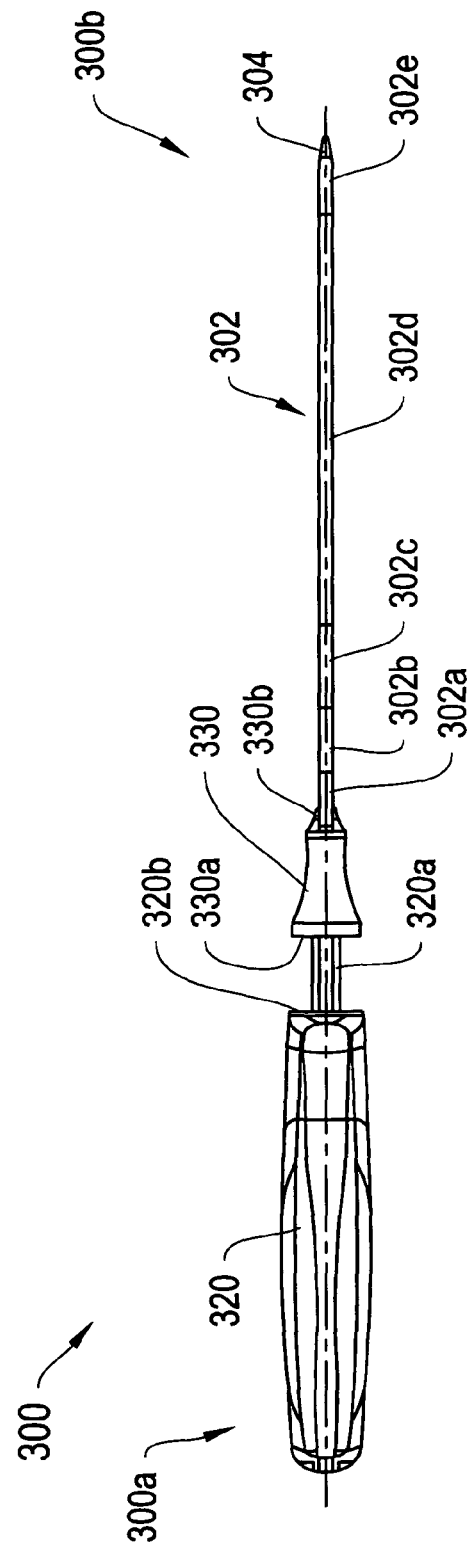

FIGS. 3A and 3B depict side and top views, respectively, of a delivery device 300 according to one embodiment of the invention. The delivery device 300 includes proximal 300a and distal 300b ends, a shaft 302, and a handle 320. Optionally, the delivery device 300 also includes a pusher assembly 330. The shaft 302 includes three straight sections 302a, 302c, and 302e, two curved sections 302b and 302d, and a conical tip 304, all lying substantially in a single plane. The first straight section 302a of the shaft 302 joins to a distal end 320b of the handle 320 and extends distally along a first axis 308. The first curved section 302b of the shaft 302 extends from a distal end of the first straight section 302a and curves away from the first axis 308. The second straight section 302c extends from a distal end of the first curved section 302b. The second curved section 302d extends from the distal end of the second straight section 302c, curves back toward the first axis 308, and terminates at a distal end. The third straight section 302e extends from the distal end of the second curved section 302d. A conical tip 304 extends distally from the third straight section 302e. In the illustrative embodiment, the shaft 302 extends across the first axis 308 a distance 382. In preferred embodiments, the distance 382 measures from about 1 cm to about 5 cm, for example from about 1.5 cm to about 4 cm. The shaft 302, at second curved section 302d, curves a maximum distance 380 from the first axis 308. In various illustrative embodiments, the distance 380 ranges from about 0.25 cm to about 2 cm. In other illustrative embodiments, the distance 380 ranges from 0.5 cm to about 1 cm.

In the illustrative embodiment, the shaft 302 is formed of surgical grade stainless steel. In some embodiments, the shaft 302 has a substantially constant diameter along its length excluding conical tip 304. In certain embodiments, the shaft 302 may have an outside diameter of less than 0.63 cm, such as less than or equal to 0.5 cm, or even less than or equal to 0.3 cm. In some embodiments, the shaft, from the distal end 320*b* of handle 320 to the distal end 300*b* of the delivery device 300 including conical tip 304, measures about 17 cm to about 23 cm in length, such as about 20 cm to about 21 cm.

The shaft 302 is sized and shaped to slidably interfit one at a time within the lumens 107*a* and 107*b* of the guide tubes 106 and 108, respectively. According to the illustrative embodiment, the shaft 302 is inserted into the lumen 107*a* or 107*b* from the inner end 106*b* or 108*b* of the guide tube 106 or 108, respectively. In alternate embodiments, the shaft 302 is inserted into the lumen 107*a* or 107*b* from the outer end 106*a* or 108*a* of the guide tube 106 or 108, respectively.

A neck portion 320*a* extends from the distal end 320*b* of the handle 320 on the first straight section 302*a*. When employed, the pusher assembly 330 slidably fits in a coaxial fashion onto the neck portion 320*a* on the first straight section 302*a* of the shaft 302. Illustratively, the pusher assembly 330 is from about 1 cm to about 5 cm in length, for example, about 3 cm in length. On grasping the handle 320, a medical operator can use a thumb to slidably position the pusher assembly 330 on the neck portion 320*a* and the first straight section 302*a*. A catch tab or other suitable mechanism can limit the distance the pusher assembly 330 may travel along the neck portion 320*a* and along the first straight section 302*a*. When the pusher assembly 300 is in its initial, retracted position, a proximal end 330*a* of the pusher assembly 330 abuts the distal end 320*b* of the handle 320. In preferred embodiments, the pusher assembly 330 snaps into a locked position when in the initial position. On grasping the handle 320, a medical operator can apply a small amount of force with her thumb on proximal end 330*a* of the pusher assembly 330 to unlock and/or unsnap the pusher assembly from the initial position. The pusher assembly 330 can be advanced distally to the advanced position over the neck portion 320*a* and/or the first straight section 302*a* a predetermined distance 322 of about 0.5 cm to about 5 cm, for example, about 2 cm, depending the length of the neck portion 320*a*.

As described in further detail below, delivery devices of the invention, such as the delivery device 300, include a handle, such as 320, and a shaft, such as 302, extending from a distal end, such as 320*b*, of the handle. The shaft 302 may include one or more substantially straight sections and/or one or more curved sections. In some configurations, the shaft 302 and the handle 320 are substantially in the same plane. In other configurations, at least one section of the shaft 302 and the handle 320 are located in different planes. In some configurations, the shaft 302 is located substantially in one plane. In other configurations, the shaft 302 includes sections located in different planes. Preferably, the section(s) of the shaft 302 that extend into the patient's body are located substantially in a single plane. The shaft 302 may be, for example, any suitable needle, cannula, tubular member, tunneler, dilator, or the like.

In one illustrative embodiment, the shaft 302 is formed from a rigid material, for example, a metal or a polymeric material. Examples of suitable metals include, but are not limited to, stainless steel, titanium, and alloys such as nitinol. Suitable polymers, which can be used as a coating on a metal to form the shaft 302, include but are not limited to, plastics such as polytetrafluoroethylene (PTFE). In other configurations, the shaft 302 has some flexibility, and can be described as semi-rigid. As described above, the shaft 302 may have a conical tip 304 at the distal end. The conical tip 304 may be configured for percutaneous punctuation and/or advancement through tissue. The tip 304 may be blunt or sharp. A blunt tip provides some resistance to unintended penetration through tissue or organ, such as the bladder.

The shaft 302 may be solid or hollow. If the shaft 302 is at least partly hollow, it may include a lumen (not shown) that has one or more openings in the shaft, for example, at the distal tip or along the side of the shaft. The cross-section of the shaft 302 may have a constant shape and size, or its shape and size may vary along its length. The cross-section of the shaft 302 may assume any suitable shape, for example, circular, semi-circular, oval, triangular, or rectangular. In other embodiments, the shaft 302 may have a distal end which may include an enlarged, flared portion to dilate tissue beyond the typical diameter of the shaft.

In one illustrative embodiment, the surface of the shaft 302 is smooth. However, the surface of the shaft 302 may be coated with one or more drugs such as anesthetic, anti-inflammatory, coagulating, anticoagulating, antibiotic, or antimicrobial agents. The drug may be delivered to the patient's tissue while the shaft 302 is in contact with the tissue. The surface of the shaft 302 may be coated with a light-absorbing coating to reduce glare, for example, under a cystoscope. The coating may be a polymer, such as Teflon, or other suitable material, and may be colored to aid in detection. The surface of the shaft 302 may be painted so that one can easily tell it apart from surrounding tissue and fluid under a cystoscope to make it easier to detect under the cystoscope. In other illustrative embodiments, the shaft 302 is textured, for example, by stippling, to provide increased traction relative to a gloved hand of a medical operator. In another illustrative embodiment, the shaft 302 is fitted with a colored sheath, such as a blue plastic sheath or a guide tube.

The handle 320 of the delivery device 300 may be of various configurations. In preferred embodiments, the handle 320 is of an ergonomic design and construction that reduces medical operator fatigue and discomfort, provides needed leverage and gripping surface for the user, orients the user as to the direction of the shaft 302, and/or provides fingertip or palm control over the shaft 302. The handle 320 may also be, for example, cylindrical. Cross-sections of the handle 320 may have variable diameters, for example, at least one portion of the handle may have a cross-section that is smaller than the adjacent portions of the handle to provide grooves for a medical operator to hold the handle. Alternatively, the cross-section of a handle 320 may have a decreasing area from the proximal end to the distal end of the handle. The handle 320 may have a substantially hexagonal cross-section. Alternatively, the handle 320 may be substantially T-shaped, D-shaped or kidney-shaped. Alternatively, the handle 320 may be a ratchet type.

The features described above for the delivery device 300 can be combined and/or incorporated into illustrative embodiments of the delivery devices 800, 900, and 1000, which are described in more detail below. Similarly, the features described above for the shaft 302 can be combined and/or incorporated into illustrative embodiments of the shafts 400, 500, 600, and 700, which are described in more detail below. Similarly, the features described above for the handle 320 can be combined and/or incorporated into illustrative embodiments of the handles 802, 902, and 1002, which are described in more detail below.

Figure 4A:
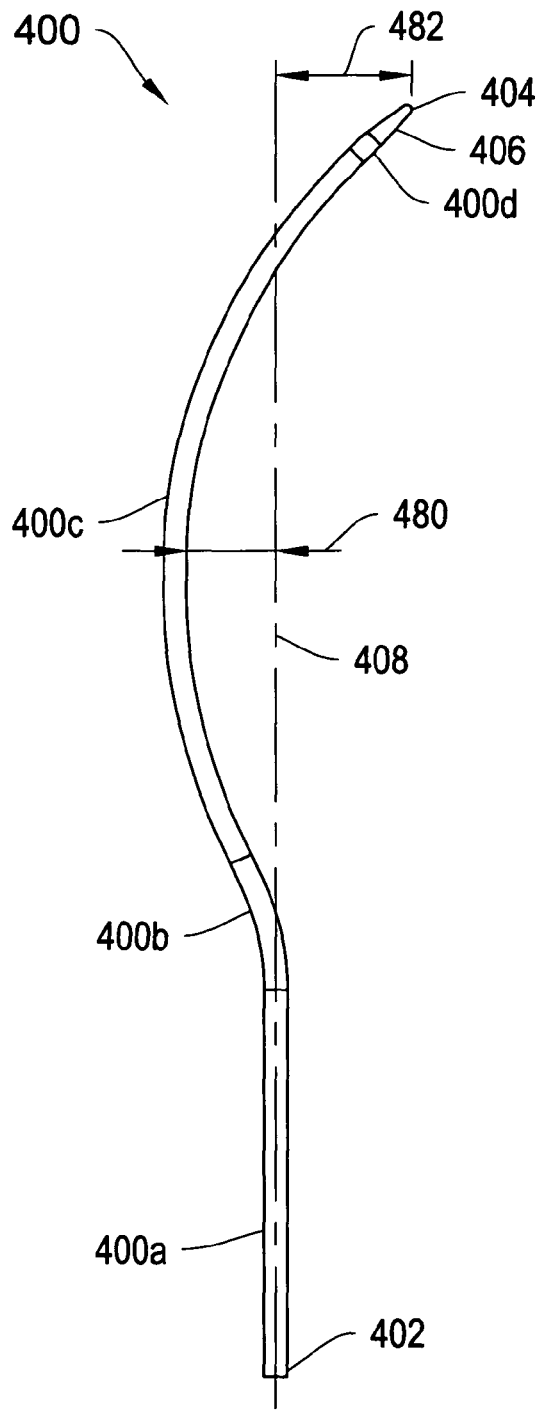
FIGS. 4A-4B depict different views of one embodiment of a shaft of a delivery device for delivering a sling to an anatomical site of a patient according to an illustrative embodiment of the invention.

FIGS. 4A-7B depict different shaft configurations illustrative of those that may be employed in a delivery device of the invention. More particularly, FIG. 4A depicts a side view of one embodiment of a shaft 400. The shaft 400 extends distally from a proximal end 402 of the shaft 400 to a distal end 404 of the shaft 400. The shaft 400 preferably has a substantially constant diameter along its length from the proximal end 402 to the distal end 404. The shaft 400 includes two straight sections 400a and 400d, and two curved sections 400b and 400c, all lying substantially in a single plane. The first straight section 400a of the shaft 400 attaches to the distal end of a handle, such as depicted in FIGS. 3A-3B and 8-10B, and extends distally along a first axis 408. The first curved section 400b of the shaft 400 extends from a distal end of the first straight section 400a and curves away from the first axis 408. The second curved section 400c extends from the distal end of the first curved section 400b, curves back toward the first axis 408, intersects the first axis 408, and terminates at a distal end extending past the intersection with the first axis 408. The second straight section 400d extends from the distal end of the second curved section 400c and terminates in a conical tip 406. In the illustrative embodiment, the shaft 400 extends across the first axis 408 a distance 482. As shown, the distance 482 is greater than the corresponding distance 382 for the shaft 302 in FIG. 3A. In other illustrative embodiments, the absolute distance 482 may be equal to or less than the distance 382, but still be a greater percentage of the overall length of the shaft 400 than the distance 382 is of the shaft 300. The shaft 400, at second curved section 400c, curves a maximum distance 480 from the first axis 408. In some illustrative embodiments, the distance 480 is relatively greater than the distance 380 for the shaft 302 in FIG. 3A.

Figure 4B:
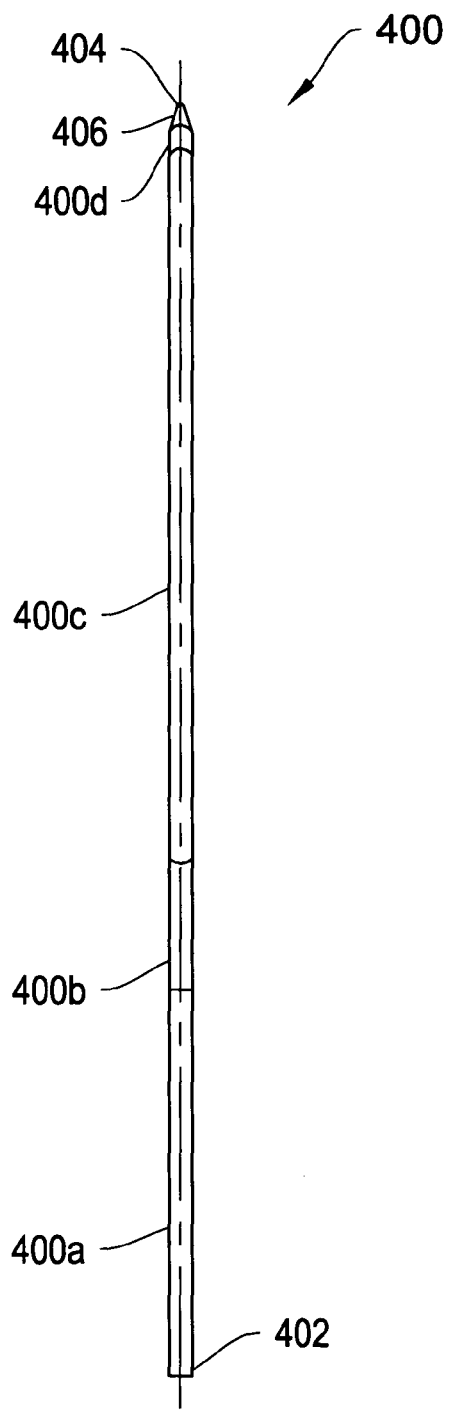

FIG. 4B depicts a top view of the shaft 400 of FIG. 4A. The shaft 400 is shown as extending substantially in one plane. The shaft 400 is about 15 cm to about 30 cm in length and about 3 mm to about 5 mm in diameter. The first straight section 400a is about 5 cm to about 8 cm in length. The first curved section 400b is about 1 cm to about 5 cm in length. The second curved section 400c is about 8 cm to about 15 cm in length. The second straight section 400d is about 1 cm to about 3 cm in length.

As discussed above in further detail with regard to FIGS. 1A-1B and 3A-3B, the guide tube 106 may be slidably fitted over the shaft 400 for associating a delivery device with a sling assembly, such as the sling assembly 100 of FIGS. 1A and 1B. Preferably, the shaft 400 is formed of surgical grade stainless steel.

FIG. 5A depicts a side view of a shaft 500 according to another illustrative embodiment of the invention. The shaft 500 extends distally from a proximal end 502 to a distal end 504 of the shaft 500. The shaft 500 preferably has a substantially constant diameter along its length from the proximal end 502 to the distal end 504. The shaft 500 includes three straight sections 500a, 500c, and 500e, and two curved sections 500b and 500d, all lying substantially in a single plane. The first straight section 500a of the shaft 500 attaches to the distal end of a handle, such as depicted in FIGS. 3A-4B and 8-10B, and extends distally along a first axis 408. The first curved section 500b of the shaft 500 extends from a distal end of the straight section 500a and curves away from the first axis 408. The second straight section 500c extends from a distal end of the first curved section 500b along a second axis at an angle to first axis 408. The second curved section 500d extends from the distal end of the second straight section 500c, curves back toward the first axis 408 and terminates before intersecting the first axis 408. The third straight section 500e extends towards first axis 408 from the distal end of the second curved section 500d and terminates in a conical tip 506 before intersecting the first axis 408. In the illustrative embodiment, the conical tip 506 is a distance 582 from intersecting the first axis 408. The shaft 500, at second curved section 500d, curves a maximum distance 580 from the first axis 408. As shown, the distance 580, with respect to the overall length of the shaft 550, is relatively greater than the distance 380 with respect to the shaft 302 in FIG. 3A.

FIG. 5B depicts a top view of the shaft 500 of FIG. 5A. The shaft 500 is shown as extending substantially in one plane. The shaft 500 is about 19 cm to about 30 cm in length and about 3 mm to about 5 mm in diameter. The first straight section 500a is about 8 cm to about 10 cm in length. The first curved section 500b is about 1 cm to about 4 cm in length. The second straight section 500c is about 4 cm to about 8 cm in length. The second curved section 500d is about 5 cm to about 8 cm in length. The third straight section 500e is about 1 cm to about 3 cm in length.

As discussed above in further detail with regard to FIGS. 1A-1B and 3A-3B, the guide tube 106 may be slidably fitted over the shaft 500 for associating a delivery device with a sling assembly, such as the sling assembly 100 of FIGS. 1A and 1B. Preferably, the shaft 500 is formed of surgical grade stainless steel.

Figure 6A:
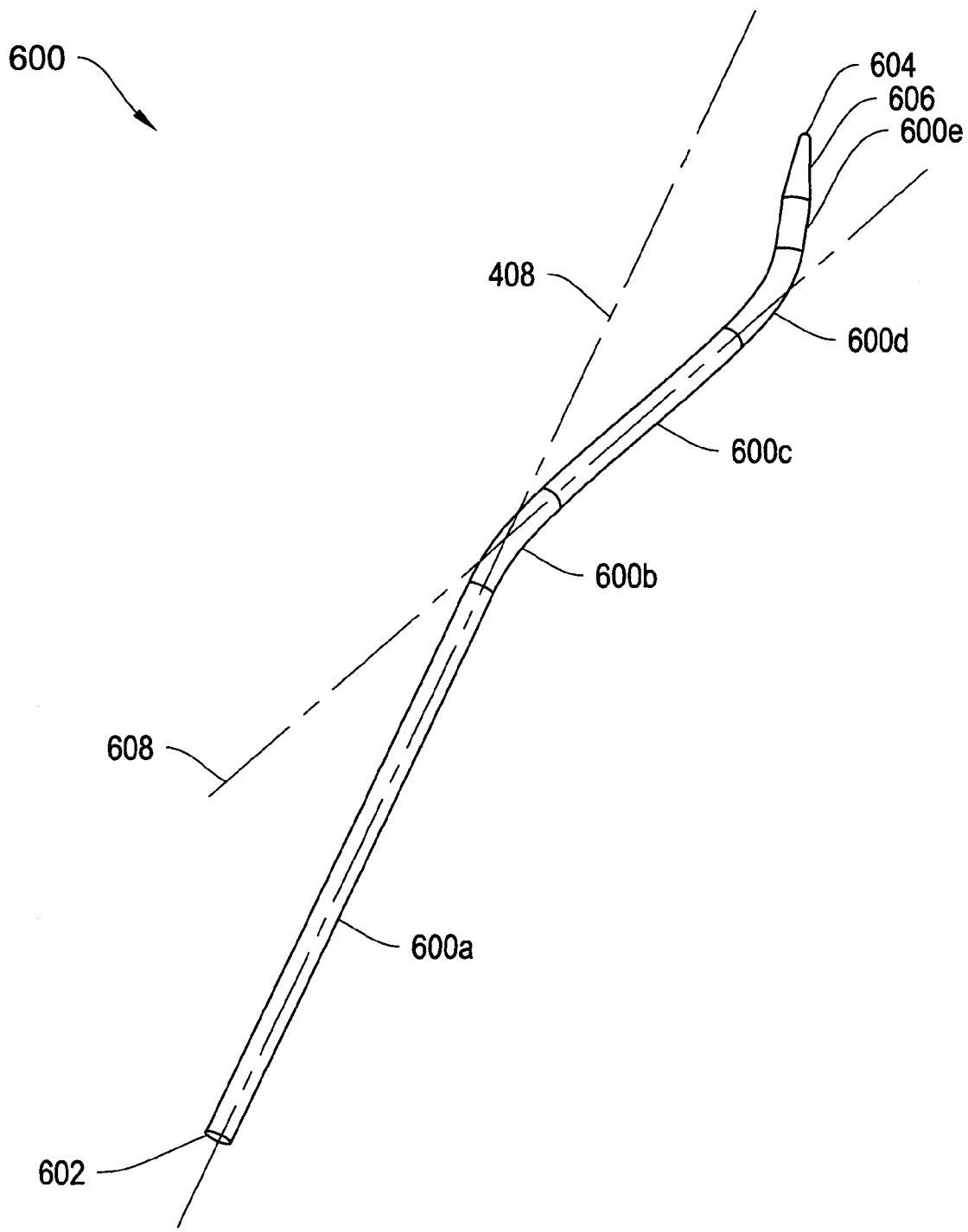
FIGS. 6A-6C depict different views of another embodiment of a shaft of a delivery device for delivering a sling to an anatomical site of a patient according to an illustrative embodiment of the invention.
Figure 6B:
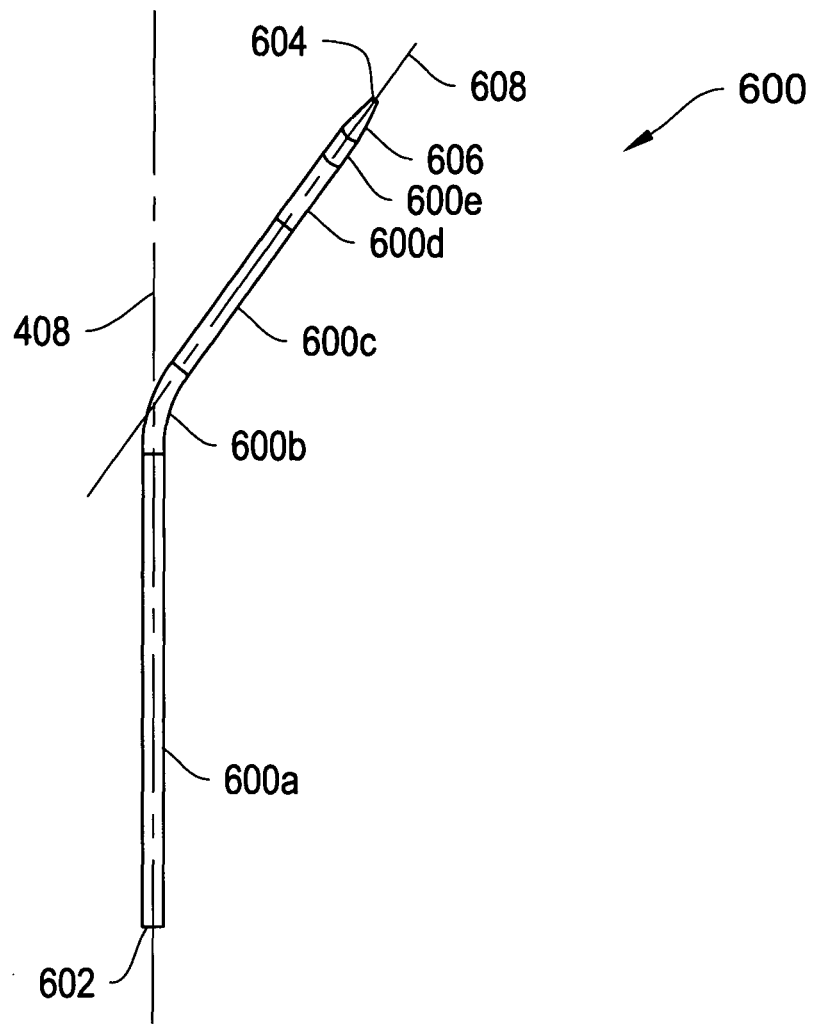
Figure 6C:
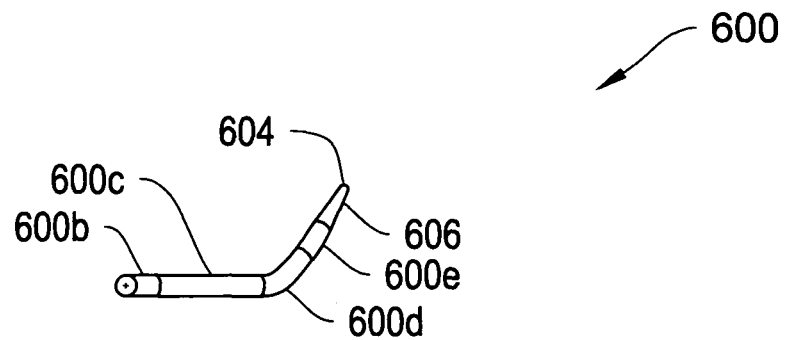

FIGS. 6A-6C depict various views of a shaft 600 according to another illustrative embodiment of the invention. The shaft 600 extends distally from a proximal end 602 to a distal end 604 of the shaft 600. The shaft 600 preferably has a substantially constant diameter along its length from the proximal end 602 to the distal end 604. The shaft 600 includes three straight sections 600a, 600c, and 600e, and two curved sections 600b and 600d. The straight sections 600a and 600c and the curved section 600b lay substantially in a first plane while the curved section 600d and the straight section 600e lay substantially in a second plane. The first straight section 600a of the shaft 600 attaches to the distal end of a handle, such as depicted in FIGS. 3A-3B and 8-10B, and extends distally along a first axis 408. A first curved section 600b of the shaft 600 extends from a distal end of the first straight section 600a and curves away from the first axis 408. A second straight section 600c of the shaft 600 extends distally along a second axis 608 from the distal end of the curved section 600b at an angle to the first axis 408. In the illustrative embodiment, the first straight section 600a, the first curved section 600b, and the second straight section 600c are substantially coplanar with each other in a first plane. A second curved section 600d of the shaft 600 extends from a distal end of the second straight section 600c and curves the shaft 600 away from the second axis 608. A third straight section 600e of the shaft 600 extends from a distal end of the second curved section 600d. The second curved section 600d and the third straight section 600e are substantially coplanar with each other in a second plane.

FIG. 6A shows a side view of the shaft 600 wherein the first plane of the first straight section 600a, the first curved section 600b, and the second straight section 600c, and the second plane of the second curved section 600d and the third straight section 600e are angled relative to each other and are not the same plane. FIG. 6B shows a view of the shaft 600 wherein the first plane of the first straight section 600a, the first curved section 600b, and the second straight section 600c is the plane of the paper. The first straight section 600a extends along the first axis 408 and the second straight section 600c extends along the second axis 608, and the first axis 408 and the second axis 608 extend at an angle with respect to each other. FIG. 6C shows a partial view of the shaft 600 wherein the second plane of the second curved section 600d and the third straight section 600e is the plane of the paper. The second straight section 600c and the third straight section 600e are angled relative to each other and may be on the second plane. The shaft 600 may be of constant cross-sectional diameter or may have differing cross-sectional diameters. Additionally, the shaft sections may have tapered cross-sectional diameters to make for smooth surface transitions from one shaft section to the next. As depicted, the shaft 600 terminates in a conical tip 606. However, any suitable tip may be employed.

In various illustrative embodiments, the shaft 600 is has a length of between about 20 cm and about 30 cm and a diameter of between about 3 mm and about 5 mm. The first straight section 600a is about 8 cm to about 10 cm in length. The first curved section 600b is about 2 cm to about 5 cm in length. The second straight section 600c is about 5 cm to about 8 cm in length. The second curved section 600d is about 2 cm to about 5 cm in length. The third straight section 600e is about 1 cm to about 3 cm in length.

As discussed above in further detail with regard to FIGS. 1A-1B and 3A-3B, the guide tube 106 may be slidably fitted over the shaft 600 for associating a delivery device with a sling assembly, such as the sling assembly 100 of FIGS. 1A and 1B. Preferably, the shaft 600 is formed of surgical grade stainless steel.

Figures 7A, 7B:
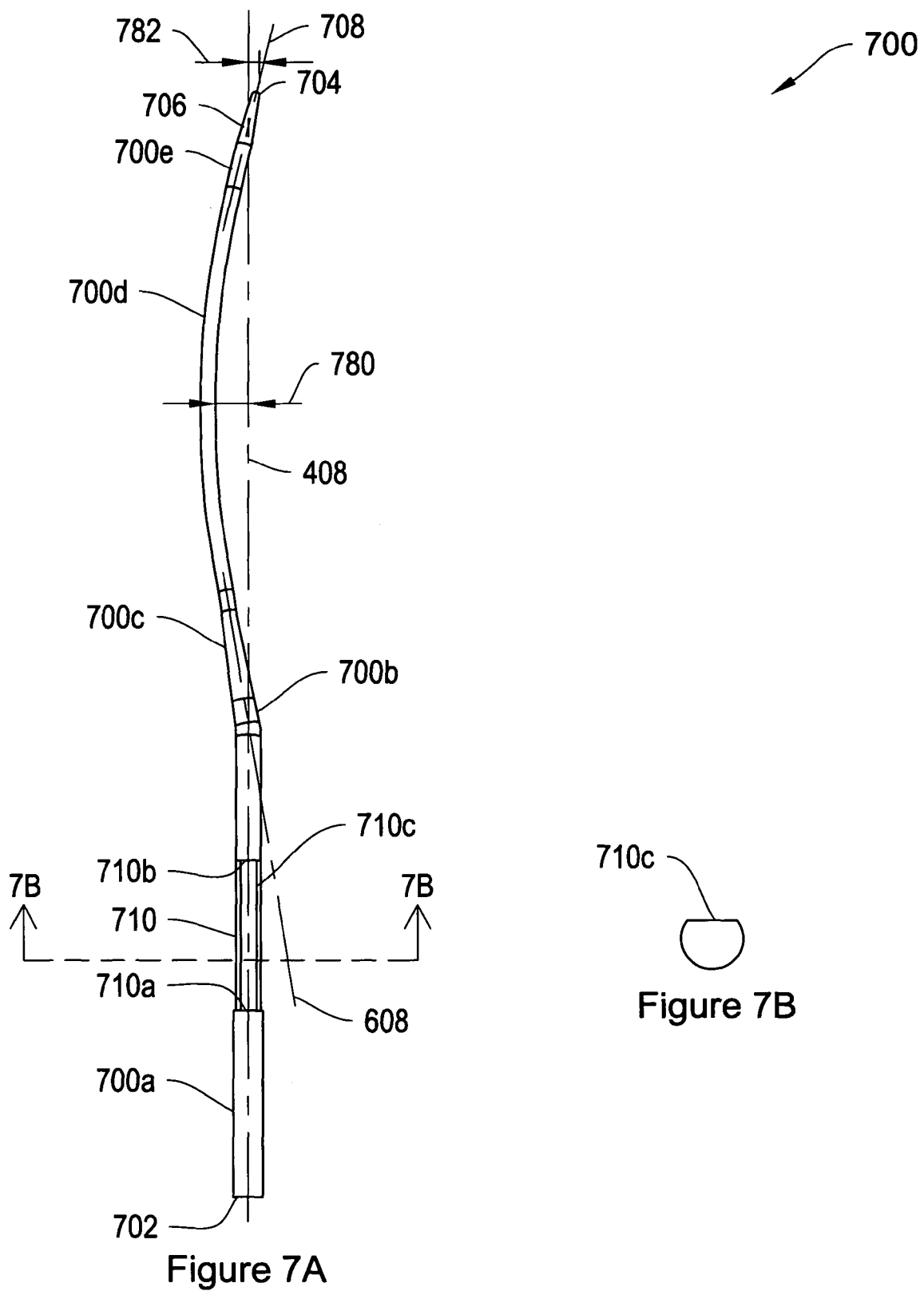
FIGS. 7A-7B depict different views of another embodiment of a shaft of a delivery device for delivering a sling to an anatomical site of a patient according to an illustrative embodiment of the invention.

FIG. 7A depicts a side view of a shaft 700 according to another illustrative embodiment of the invention. The shaft 700 extends distally from a proximal end 702 to a distal end 704 of shaft 700. The shaft 700 includes three straight sections 700a, 700c and 700e, and two curved sections 700b and 700d, all lying substantially in a single plane. A first straight section 700a of the shaft 700 attaches to the distal end of a handle, such as depicted in FIGS. 3A-3B and 8-10B, and extends distally along a first axis 408. The first straight section 700a of the shaft 700 extends distally along a first axis 408, and preferably has a substantially constant diameter, D1. A first curved section 700b of the shaft 700 extends from a distal end of the first straight section 700a, curves away from the first axis 408, and also preferably has a substantially constant diameter, D1. A second straight section 700c extends from a distal end of the first curved section 700b along a second axis 608, and preferably has a diameter that decreases from its proximal end to its distal end to provide increased structural stability to the shaft 700. A second curved section 700d preferably has a substantially constant diameter D2, smaller than the diameter D1 of the first curved section 700b and the first straight section 700a, and extends from the distal end of the second straight section 700c, curves back toward the first axis 408, and terminates at a distal end approximately at an intersection with the first axis 408. A third straight section 700e preferably has a substantially constant diameter D2 and extends from the distal end of the second curved section 700d along a third axis 708, which crosses the first axis 408. A conical tip 706 extends distally from the third straight section 700e. In the illustrative embodiment, the shaft 700 extends across the first axis 408 a distance 782. In certain embodiments, the distance 782 may be greater than, less than, or approximately equal to the distance 382 for the shaft 302 in FIG. 3A. The shaft 700, at the second curved section 700d, curves a maximum distance 780 from the first axis 408. In certain embodiments, the distance 780 may be relatively greater than, lesser than, or approximately equal to the distance 380 for the shaft 302 in FIG. 3A.

The shaft 700 is shown as having an elongated notch 710 along the first straight section 700a. FIG. 7B depicts a cross-sectional view of the shaft 700 across the line 7B in FIG. 7A. A proximal end 710a and a distal end 710b of the elongated notch 710 radially extend into the first straight section 700a and form the ends of a distally extending rectangular planar surface 710c. A pusher as discussed in detail with respect to FIG. 9 may be fitted on the elongated notch 710. The proximal end 710a and the distal end 710b of the elongated notch 710 limit the distance the pusher may travel along the first straight section of the shaft 700. One or more elongated notched sections may be included on the shafts 302, 400, 500, 600, and 700. The diameter of the straight section 700a along the rectangular planar surface 710c is smaller than the diameter of the straight section 700a not including the elongated notch 710 and may be as small as half the diameter of the diameter of the straight section 700a not including the elongated notch 710. The first straight section 700a may be about 6 mm to about 8 mm in diameter. The elongated notch 710 may extend from about 2 cm to about 8 cm from its proximal end 710a to its distal end 710b.

The shaft 700 is about 13 cm to about 33 cm in length. The first straight section 700a is about 8 cm to about 10 cm in length and about 4 mm to about 8 mm in diameter. The first curved section 700b is about 1 cm to about 3 cm in length and about 4 mm to about 8 mm in diameter. The second straight section 700c is about 2 cm to about 8 cm in length, and has a first diameter D1 of about 4 mm to about 8 mm at its proximal end and a second diameter D2 of about 3 mm to about 5 mm at its distal end. The second curved section 700d is about 5 cm to about 10 cm in length and has a diameter of about 3 mm to about 5 mm. The third straight section 700e is about 1 cm to about 3 cm in length and has a diameter of about 3 mm to about 5 mm.

As discussed above in further detail with regard to FIGS. 1A-1B and 3A-3B, the guide tube 106 may be slidably fitted over the shaft 700 for associating a delivery device with a sling assembly, such as the sling assembly 100 of FIGS. 1A and 1B. Preferably, the shaft 700 is formed of surgical grade stainless steel.

Figure 8:
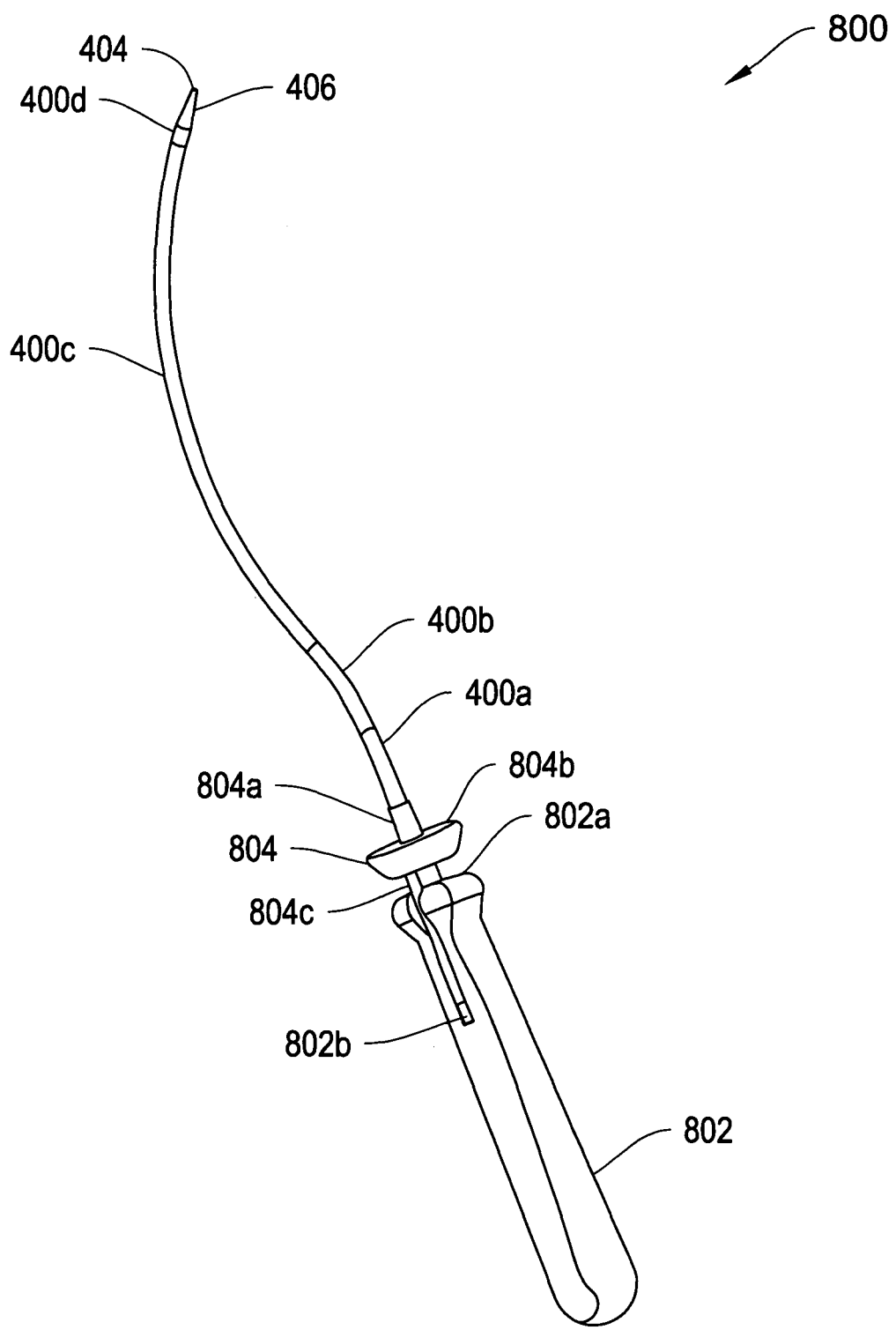
FIG. 8 depicts a side view of another embodiment of a delivery device for delivering a sling to an anatomical site of a patient according to an illustrative embodiment of the invention.

FIGS. 8-10B depict different illustrative embodiments of handles and pushers according to the invention. More particularly, FIG. 8 depicts a side view of a delivery device 800 according to an illustrative embodiment of the invention. The delivery device 800 includes a handle 802 and the shaft 400 of FIGS. 4A-4B extending distally from a distal end 802a of the handle 802. The handle 802 includes a notch 802b. A pusher 804 slidably sits on the first straight section 400a of the shaft 400 and is formed of a neck section 804a, a ring 804b, and a strut 804c. The ring 804b is used to position the pusher 804 on the first straight section 400a. The strut 804c mates with the notch 802b in the handle 802 and includes at least one additional feature, such as a stop tab, to limit the distance the pusher 804 may travel along the first straight section 400a. In its initial position, the pusher 804 abuts the distal end 802a of the handle 802. When extended, for example, by a medical operator during an implantation procedure, the pusher 804 may be pushed a predetermined distance of about 1 cm to about 5 cm, depending the length of the strut 804c.

Figure 9:
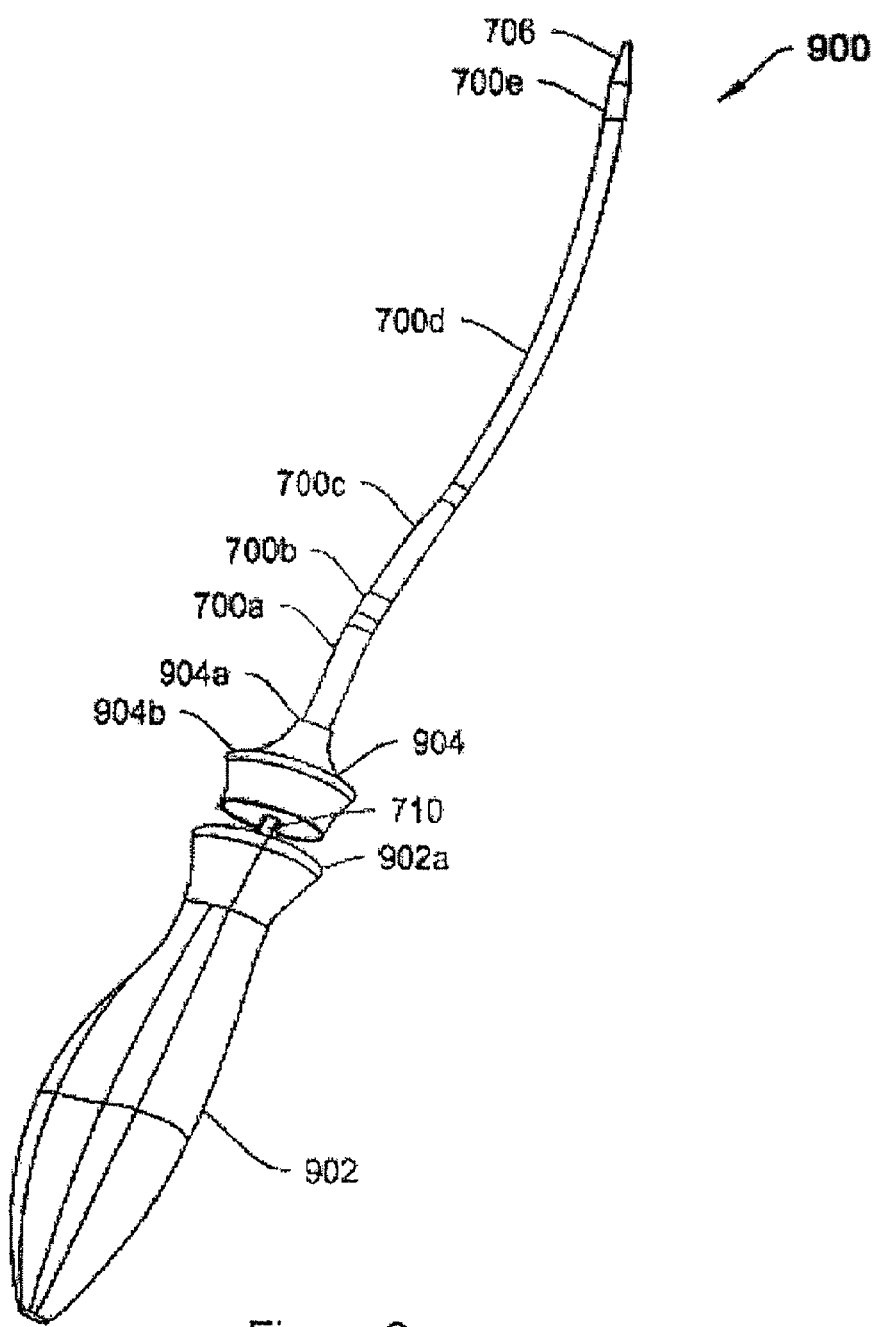
FIG. 9 depicts a side view of another embodiment of a delivery device for delivering a sling to an anatomical site of a patient according to an illustrative embodiment of the invention.

FIG. 9 depicts a side view of a delivery device 900 according to an illustrative embodiment of the invention. The delivery device 900 includes a handle 902 and the shaft 700 of FIG. 7A extending distally from a distal end 902a of the handle 902. Optionally, a pusher 904 slidably fits onto the elongated notch 710 on the first straight section 700a of the shaft 700 and is formed of a neck section 904a and a ring 904b. The ring 904b is used to position the pusher 904 on the delivery device 900. The proximal 710a and distal 710b ends of the elongated notch 710 limit the distance the pusher 904 may travel along the first straight section 700a. In its initial position, the pusher 904 abuts the distal end 902a of the handle 902. When extended, for example, by a medical operator during an implantation procedure, the pusher 904 may be pushed a predetermined distance of about 1 cm to about 5 cm, depending the length of elongated notch 710.

Figure 10A:
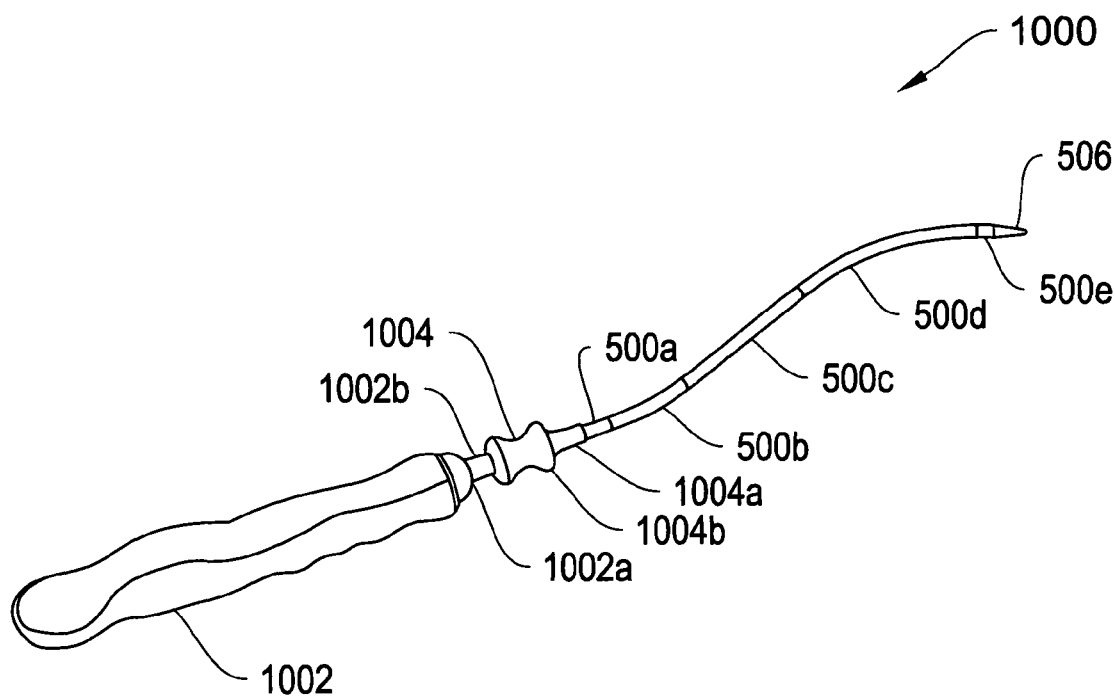
FIGS. 10A and 10B depict different views of another embodiment of a delivery device for delivering a sling to an anatomical site of a patient according to an illustrative embodiment of the invention.
Figure 10B:
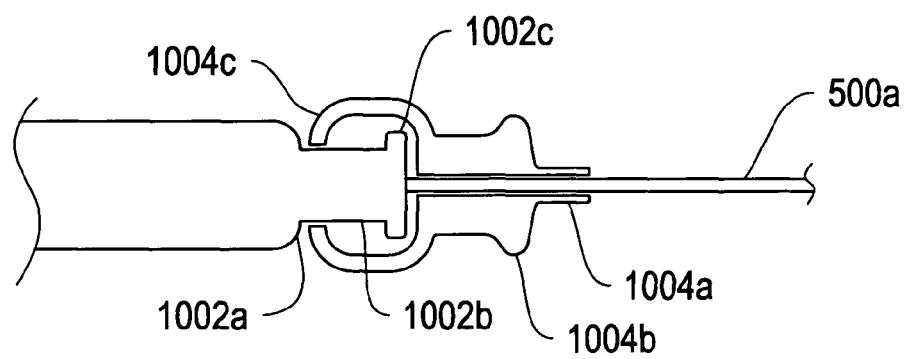

FIG. 10A depicts a side view of a delivery device 1000 according to an illustrative embodiment of the invention. The delivery device 1000 includes a handle 1002 and the shaft 500 of FIG. 5 extending distally from a distal end 1002a of the handle 1002. A neck portion 1002b extends from the distal end 1002a of the handle 1002 on the first straight section 500a. The neck portion 1002b ends in a tab 1002c as shown in FIG. 10B. A pusher 1004 is slidably fitted onto the neck portion 1002b on the first straight section 500a of the shaft 500 and is formed of a neck section 1004a, a ring 1004b, and a tab 1004c. The ring 1004b is used to slidably position the pusher 1004 on the neck portion 1002b and the first straight section 500a. The tab 1002c of the handle 1002 and the tab 1004c of the pusher 1004 limit the distance the pusher 1004 may travel along the first straight section 500a. In its initial position, the pusher 1004 abuts the distal end 1002a of the handle 1002. When extended, for example, by a medical operator during an implantation procedure, the pusher 1004 may be pushed a predetermined distance of about 1 cm to about 5 cm, depending the length of the neck portion 1002b.

FIG. 10B shows a detailed cross-sectional view of the neck portion 1002b, the tab 1002c, and the pusher 1004. In its retracted position, the tab 1004c of the pusher 1004 contacts the distal end 1002a of the handle 1002. When the pusher 1004 is fully extended or pushed, the tab 1004c of the pusher 1004 contacts the tab 1002c of the handle 1002 and prevents the tab 1004c, and thus, also prevents the pusher 1004, from extending further.

It should be understood that each of shafts 302, 400, 500, 600, and 700 may be used in combination with each of the above mentioned pusher assemblies and handles, or may be employed without pusher assemblies. FIGS. 3A-3B and 8-10B illustrate specific combinations of shafts, pushers, and handles, and are not met to be limiting.

Any of the delivery devices and shafts described above may be employed to create a passage through body tissue, for example, from the vagina over the topside of the pubic bone and to the abdominal wall or the reverse according to the methodologies described herein. Any of the delivery devices described above may be used to deliver and place any suitable implant, such as a sling (e.g., a knitted mesh), or a sling assembly, at an anatomical site in the body of a patient. Additionally, any suitable mechanism may be employed to associate the sling assembly with the shaft of the delivery device. According to the illustrative embodiment, the sling assembly does not affix, attach, connect or join with the shaft of the delivery device(s). Instead, it slides onto the delivery device in a removable fashion.

Without limitation, exemplary sling assembly configurations that may be operable with illustrative embodiments of the invention may be found in U.S. patent application Ser. No. 10/642,395; U.S. patent application Ser. No. 10/641,170; U.S. patent application Ser. No. 10/641,192; U.S. Provisional Patent Application Ser. No. 60/495,439, U.S. patent application Ser. No. 10/640,838; U.S. Provisional Patent Application Ser. No. 60/403,555; U.S. Provisional Patent Application Ser. No. 60/465,722; U.S. patent application Ser. No. 10/460; 112; and U.S. patent application Ser. No. 09/096,983, the entire contents of all of which are incorporated herein by reference.

Figure 11:
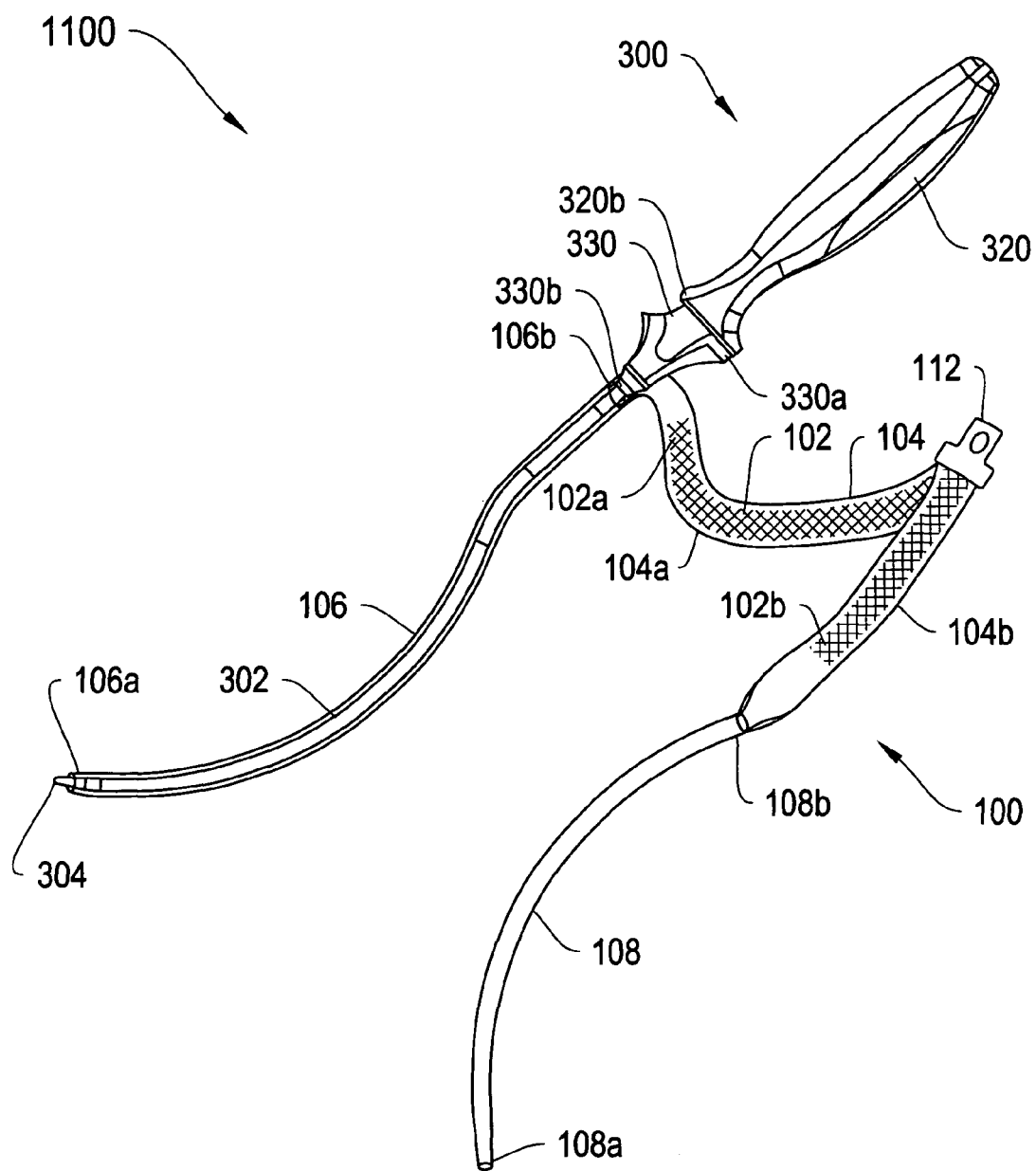
FIG. 11 depicts a perspective side view of an assembled sling delivery system including the sling assembly of FIGS. 1A-1B and the delivery device of FIGS. 3A-3B, according to one embodiment of the invention.

FIG. 11 depicts a sling delivery system 1100 where the sling assembly 100 of FIGS. 1A-1B is employed with delivery device 300 of FIGS. 3A-3B. The two guide tubes 106 and 108 slidably fit over the conical tip 304 and along the length of the shaft 302 one at a time. According to one feature, the guide tubes 106 and 108 and the shaft 302 are sized and shaped such that when the pusher assembly 330 is in the initial, retracted position, as shown in FIG. 11, the inner guide tube end 106b or 108b abuts the distal end 330b of the pusher assembly 330, and the conical tip 304 extends beyond the outer guide tube end 106a or 108a. When the conical tip 304 extends beyond the outer guide tube end 106a or 108a it is exposed for tissue piercing and/or tunneling. When the medical operator pushes the pusher assembly 330 into the advanced position, the distal end 330b of the pusher assembly 330 pushes on the inner end 106b or 108b of guide tube 106 or 108, and the outer guide tube end 106a or 108a moves distally past the conical tip 304 and becomes accessible for removal from the shaft 302. During removal, the medical operator grasps the outer guide tube end 106a or 108a, either by hand, or using forceps or a hemostat and pulls in a proximal direction on the delivery device 300, thus removing the shaft 302 from the guide tube 106 or 108. As noted above with regard to other illustrative embodiments, the delivery system 1100 need not include a pusher assembly 330. Instead, the medical operator may grasp or otherwise temporarily anchor the outer guide tube end 106a or 108a and withdraw the delivery device 300 in a proximal direction to remove the shaft 302 from the guide tube, without first advancing the guide tube end 108a or 106b distally past the conical tip 304 of the shaft 302.

Figure 12A:
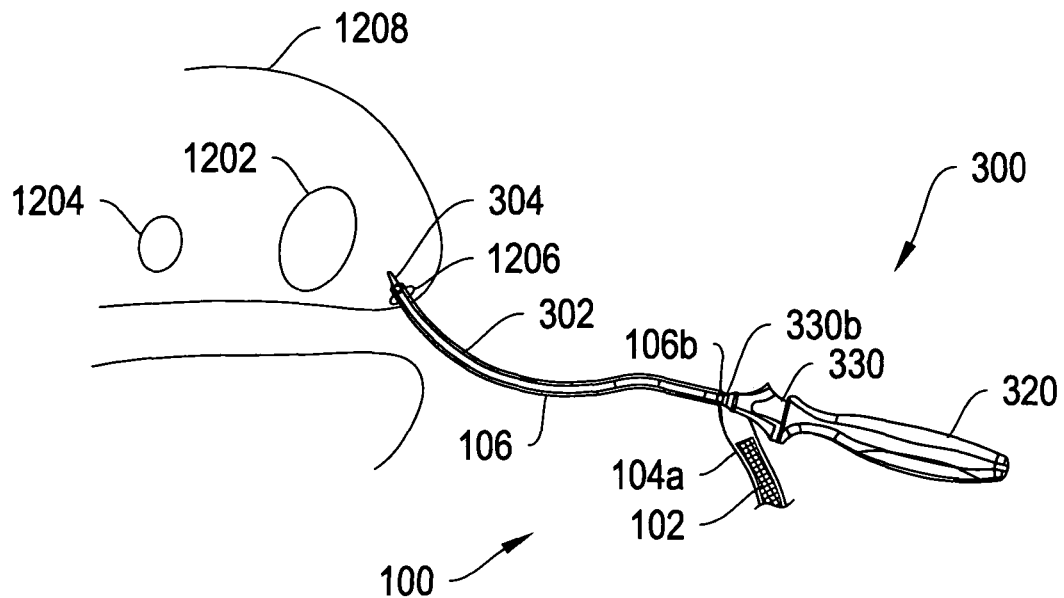
FIGS. 12A-12E depict schematic views of steps in a transvaginal, prepubic approach for delivering a sling to an anatomical site of a female patient using the sling delivery system of FIG. 11.

FIGS. 12A-12E depict schematic views of steps in a transvaginal, prepubic approach for delivering an implant, such as the sling 102 or the sling assembly 100, to an anatomical site, such as a urethra, in the body of a patient using sling delivery system 1100 of FIG. 11. In use, the illustrative shaft 302, fitted with the sling assembly 100 via the guide tube 106, is employed to create passages through body tissue, namely, from the vagina to the abdomen. Two incisions 1208a and 1208b on each side of the midline of the body are made in the lower abdomen and an incision 1206 is made in the vaginal wall. FIG. 12A depicts a side view of the conical tip 304 of the shaft 302 entering the vaginal incision 1206. The conical tip 304 of the shaft 302 is inserted into the vaginal incision at an angle of about 20 degrees to the left or right of the vertical midline of the body of the patient. According to the illustrative embodiment, after about 5 cm to about 8 cm of the shaft 302 is inserted into the patient and contacts the pubic bone 1202, the handle 320, and thus the shaft 302, is rotated clockwise or counterclockwise about 180 degrees. However, in alternative illustrative embodiments, depending on the shape of the shaft 302, the handle 320 may be rotated about 30 degrees, about 60 degrees, about 90 degrees, or not rotated substantially.

Figure 12B:
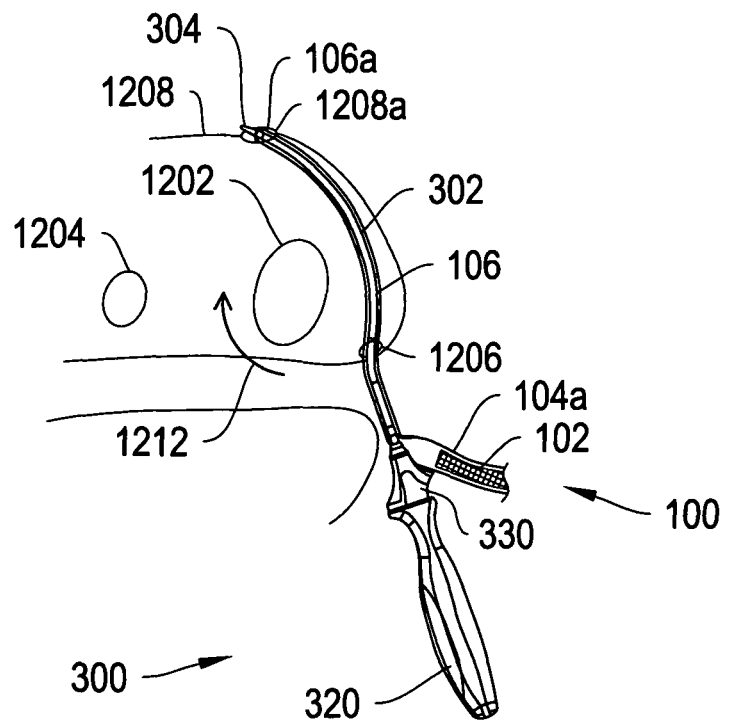

FIG. 12B depicts a side view of the shaft 302 turning about 180 degrees about the axis of the handle 320, advancing above and along an anterior surface of the pubic bone 1202 and tunneling through the body of the patient toward the abdominal wall 1208. During this time or at other times during the procedure, the medical operator may more accurately guide advancement of the shaft 302 by feeling one or more portions of shaft 302 under the surface of the skin of the patient. The shaft 302 continues to tunnel through the body tissues of the patient until the conical tip 304 of the shaft 302 and the outer end 106a of the guide tube 106 extend through one of the abdominal incisions 1208a or 1208b in the abdominal wall 1208. Then the medical operator advances the pusher assembly 330 distally away from the handle 320 to the advanced position, advancing the outer end 106a of the guide tube 106 beyond the conical tip 304 of the shaft 302. The medical operator then temporarily secures the guide tube outer end 106a extra-abdominally, for example with a clamp or hemostat, and the shaft 302 is carefully withdrawn from the guide tube 106 and out from the body from the vaginal incision 1206. If the outer end 106a of the guide tube 106 retracts back into the abdomen, the shaft 302 can be advanced through the lumen 107a of the guide tube 106 to reseat the guide tube. The above process can then be repeated until the conical tip 304 of the shaft 302 and the outer end 106a of the guide tube 106 extend extra-abdominally through one of the abdominal incisions 1208a or 1208b. The mirror image of the above described process is then repeated using delivery device 300 with the guide tube 108 on the contra-lateral side of the body.

In other illustrative embodiments, the guide tube 106 may be completely or almost completely withdrawn from the body through the abdominal incision 1208a before the delivery device 300 is used to introduce the guide tube 108 into the body. In other illustrative embodiments, a second delivery device similar to the delivery device 300 may be used to introduce the guide tube 108 into the body. Following withdrawal of the shaft 302 from either guide tube 106 or 108, the medical operator may perform a cystoscopy if desired. However, the above described prepubic approach for introduction of the shaft 302 into the body of the patient reduces the possibility of damage to the internal organs of the patient, for example from puncturing of the bladder 1204 by the shaft 302, which may occur during a suprapubic approach along the path marked by the arrow 1212. This improvement reduces the need to perform a cystoscopy to verify placement.

Figure 12C:
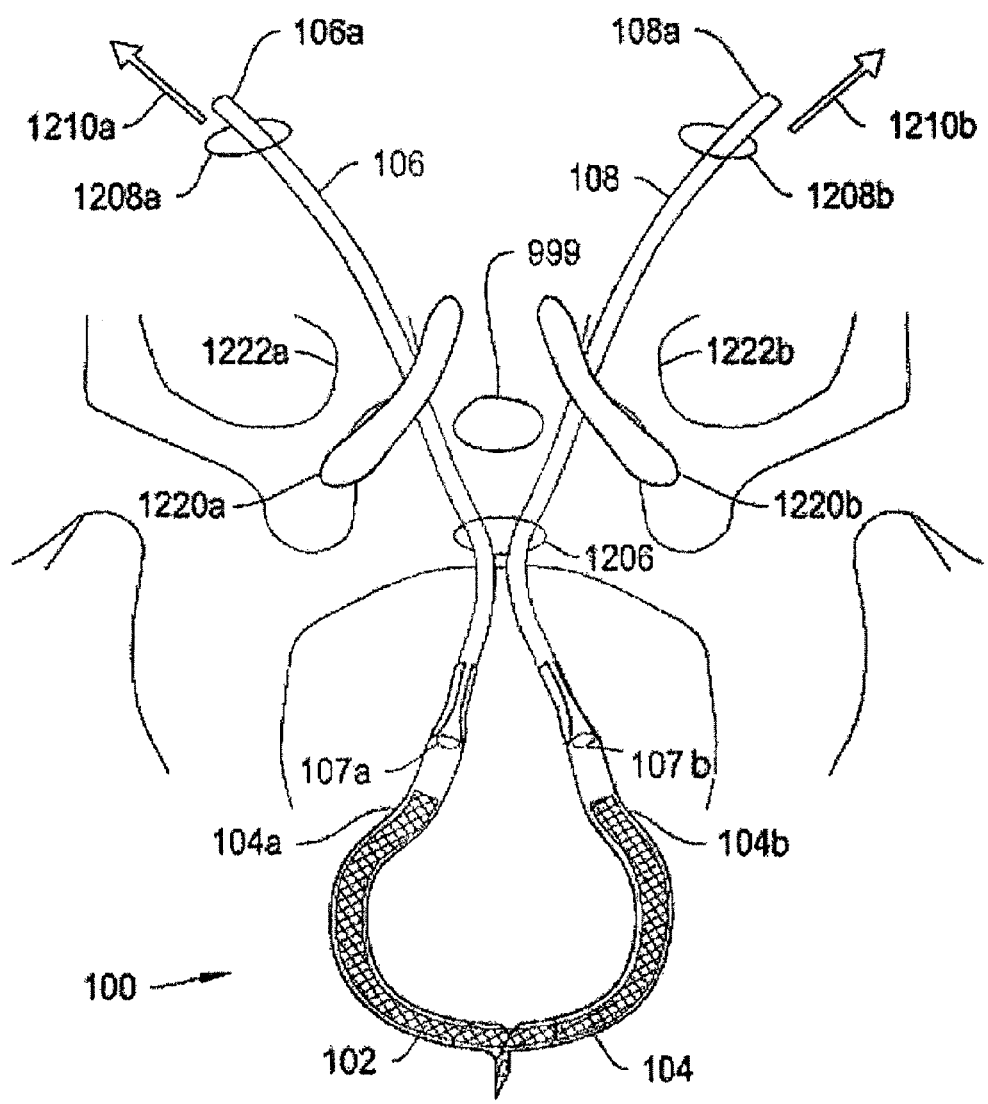
Figure 12D:
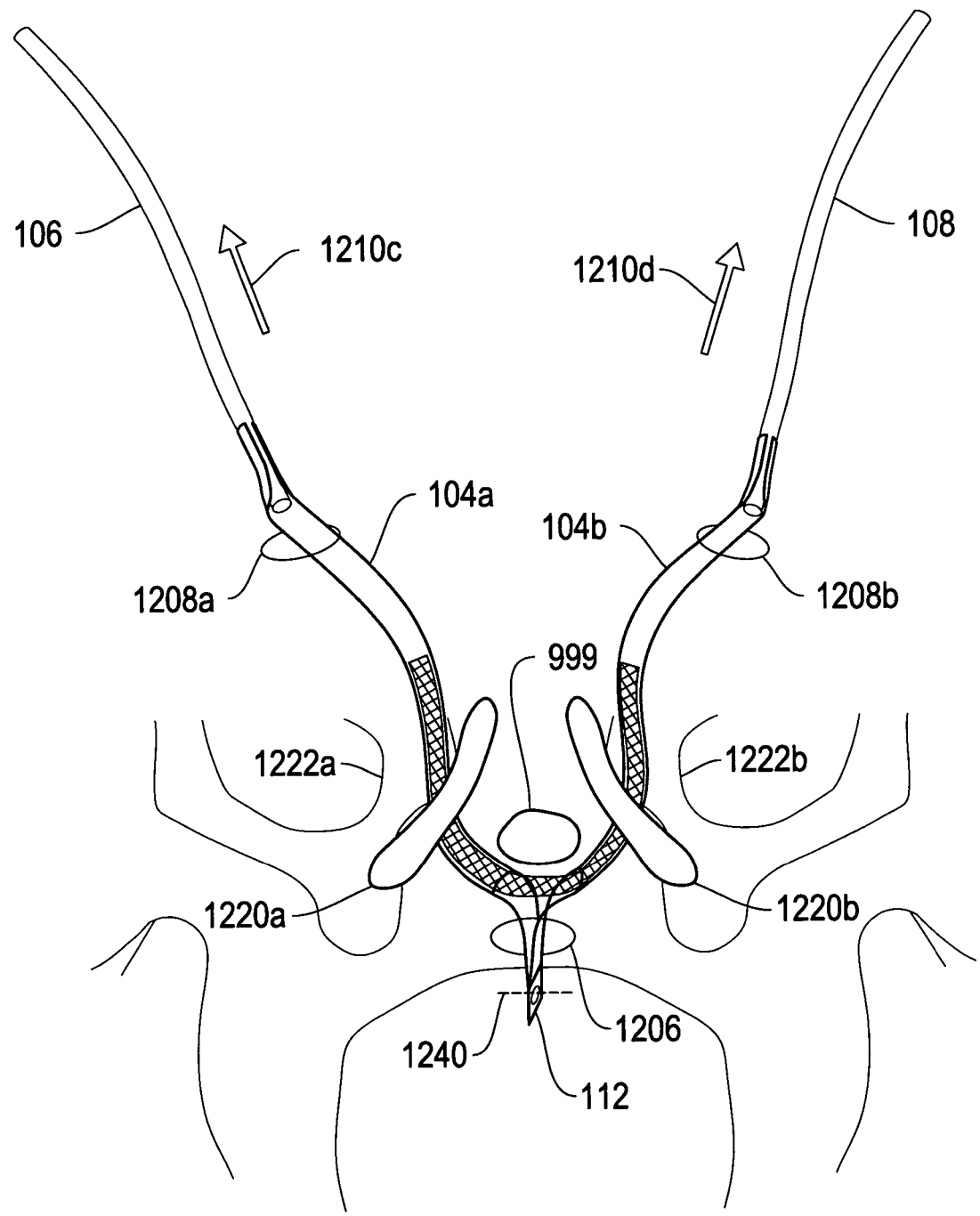
Figure 12E:
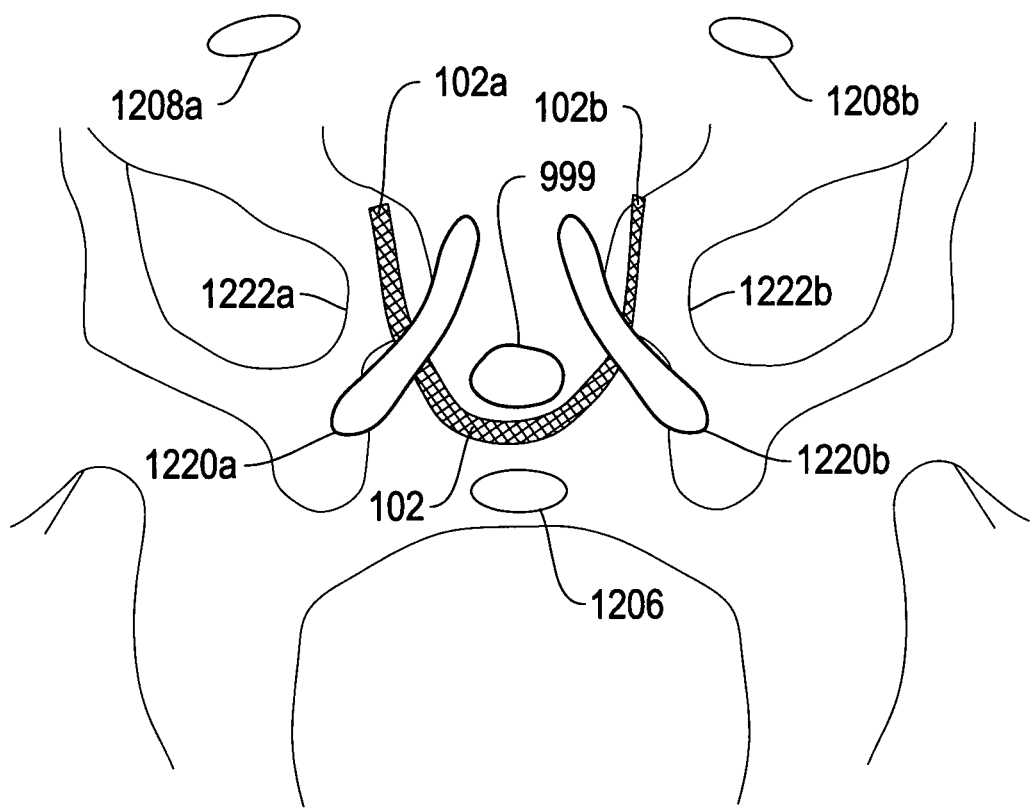

FIGS. 12C-E depict a front view of the above trans-vaginal, prepubic approach for delivering the sling 102 and/or the sling assembly 100 to an anatomical site in the body of a patient. As shown in the illustrative embodiment, the guide tube 106 is inserted to the left of the urethra 999. Similarly, guide tube 108 is inserted to the right of urethra 999. According to the illustrative embodiment, the guide tube 106 is introduced between the ischiocavernous pubic muscle 1220a and ischiopubic bone 1222a. Similarly, the guide tube 108 is introduced between the ischiocavernous pubic muscle 1220b and ischiopubic bone 1222b.

Next, the guide tubes 106 and 108 are pulled out from their respective abdominal incisions 1208a and 1208b in the direction of the arrows 1210a and 1210b, respectively. As shown in FIG. 12D, removal of the guide tubes 106 and 108 draws each sleeve portion 104a and 104b of the sling assembly 100 through the respective passages previously created by the shaft 302 and the guide tubes 106 and 108. The guide tubes 106 and 108 may be used as handles to adjust the position of the sling assembly 100 to achieve desired placement. Also, the tab 112 can be used during implantation as a visual aid for placement of the sling 102 and/or sling assembly 100 to the desired location in the body of the patient, such as centered below the urethra 999. If necessary, the guide tube 106 and/or 108 may be rotated one or more times to relieve twisting or other deformations in the sling 102 and/or the sling assembly 100 that may have occurred during placement. In one illustrative embodiment, the sleeve portion 104a is introduced between the ischiocavernous pubic muscle 1220a and ischiopubic bone 1222a, and the sleeve portion 104b is introduced between the ischiocavernous pubic muscle 1220b and ischiopubic bone 1222b.

In embodiments employing a sleeve 104, once desired placement of the sling assembly 100 is achieved, the tab 112 is cut, along dotted line 1240, across the indentations 112e and the aperture 112g, to separate the sleeve portions 104a and 104b. By pulling on the guide tubes 106 and 108 in the direction of the arrows 1210c and 1210d, respectively, the sleeve portions 104a and 104b are slid off the sling 102 and removed from the body, and the sling 102 is placed in position under the urethra 999, as depicted in FIG. 12E. The sleeve portions 104a and 104b and the guide tubes 106 and 108 are then discarded. In some illustrative embodiments, the sling 102 is anchored between the ischiocavernous pubic muscles 1220a and 1220b and ischiopubic bones 1222a and 1222b, as shown in the illustrative embodiment. Optionally, the ends 102a and 102b of sling 102 may be cut to a desired length. In other illustrative embodiments, the sling ends may be anchored in any suitable location or may be left unanchored.

Unless stated otherwise herein, the various components of the invention are made of biocompatible and/or materials, which can include, for example, poly-alpha-hydroxy acids (e.g. polylactides, polyglycolides and their copolymers), polyanhydrides, polyorthoesters, segmented block copolymers of polyethylene glycol and polybutylene terephtalate (Polyactive™), tyrosine derivative polymers or poly(esteramides), polyethylene/ethylene vinyl acetate (EVA) blend, polyethylene, polyester, nylon, polypropylene, thermoplastic fluorinated ethylene propylene (FEP), TFP, stainless steel, malleable metal or any combination of these materials. In certain embodiments, the delivery systems of the invention include cadaveric, animal, and/or autologous human tissue Many variations, modifications, other implementations, and equivalents of what is described herein exist and do not depart from the spirit and the scope of the invention. For example, all operative combinations between the above described illustrative embodiments and those features described in the documents incorporated by reference herein are considered to be potentially patentable embodiments of the invention.

What is claimed is:

1. A sling delivery system comprising:
a sling assembly, having first and second sling assembly ends, including, an implantable sling, sized and shaped for providing a urethral platform, and first and second guide tubes integrally attached to the sling assembly and having inner and outer ends, wherein the outer end of each of the first and second guide tubes are located at the first and second sling assembly ends, respectively; and
a first delivery device including a handle having proximal and distal ends, and a shaft attached at the distal end of the handle and having a length that extends distally from the distal end of the handle inclusive of a conical tip on a single plane; wherein the shaft includes a first substantially straight section extending along a first axis from the distal end of the handle, a first curved section that curves away from the first axis and a second curved section that curves back toward the first axis, the shaft also including a distal portion that extends between about 1 cm and about 5 cm back across the first axis;
wherein the shaft is shaped for delivering the sling via a trans-vaginal, prepubic approach, the inner end of the first guide tube is sized and shaped for slidably interfitting over the distal end of the shaft, and the first guide tube has an outer end that is tapered; and
a pusher assembly slidably fitted over the shaft and extending along a portion of a length of the shaft, wherein when the first guide tube is interfitted over the shaft, the inner end of the first guide tube abuts a distal end of the pusher assembly, such that when the pusher assembly is in a first position the conical tip of the first delivery device is exposed, and when the pusher assembly is in an advanced position, the outer end of the first guide tube moves distally past the conical tip of the first delivery device.

2. The sling delivery system of claim 1, wherein the inner end of the second guide tube is sized and shaped for interfitting, alternating with the first guide tube, over the shaft.

3. The sling delivery system of claim 1, wherein the sling assembly includes a protective sleeve for covering, at least partially, the supportive sling, and wherein the inner ends of the first and second guide tubes attach integrally to first and second ends, respectively, of the protective sleeve.

4. The sling delivery system of claim 3, wherein the protective
sleeve includes a gap in a top side exposing a portion of the supportive sling across a substantial portion of its width, the gap being between about 1 cm and about 3 cm.

5. The sling delivery system of claim 1, comprising:
a second delivery device including, a handle having proximal and distal ends, a shaft attached at and extending distally from the distal end of the handle, and a pusher assembly slideably fitted over the shaft and extending distally along a portion of a length of the shaft from near the proximal end of the shaft and actuatable along a portion of the shaft, wherein the inner end of the second guide tube is sized and shaped for interfitting over the shaft and abutting the distal end of the pusher assembly of the second delivery device.

6. The sling delivery system of claim 1, wherein the first and second guide tubes have an inside diameter of less than about 0.63 cm.

7. The sling delivery system of claim 1, wherein the first and second guide tubes have an insider diameter of less than or equal to about 0.5 cm.

8. The sling delivery system of claim 1, wherein the first and second guide tubes have an inside diameter of less than or equal to about 0.3 cm.

9. The sling delivery system of claim 1, wherein the shaft, exclusive of the conical tip, has a substantially constant outside diameter of less than about 0.5 cm.

10. The sling delivery system of claim 1, wherein the shaft, exclusive of the conical tip, has a substantially constant outside diameter of less than about 0.3 cm.

\* \* \* \* \*